United States Patent
Buelna

(10) Patent No.: US 12,279,800 B2
(45) Date of Patent: Apr. 22, 2025

(54) METHODS AND DEVICES FOR TREATING POLYCYSTIC KIDNEY DISEASE AND ITS SYMPTOMS

(71) Applicant: Verve Medical, Inc., Peoria, AZ (US)

(72) Inventor: Terrence J. Buelna, Scottsdale, AZ (US)

(73) Assignee: Verve Medical, Inc., Paradise Valley, AZ (US)

( * ) Notice: Subject to any disclaimer, the term of this patent is extended or adjusted under 35 U.S.C. 154(b) by 1008 days.

(21) Appl. No.: 17/143,725

(22) Filed: Jan. 7, 2021

(65) Prior Publication Data

US 2021/0121218 A1  Apr. 29, 2021

Related U.S. Application Data

(63) Continuation-in-part of application No. 17/016,232, filed on Sep. 9, 2020, now abandoned, which is a
(Continued)

(51) Int. Cl.
*A61B 18/14* (2006.01)
*A61B 18/00* (2006.01)
(Continued)

(52) U.S. Cl.
CPC .............. *A61B 18/00* (2013.01); *A61B 18/08* (2013.01); *A61B 18/1492* (2013.01);
(Continued)

(58) Field of Classification Search
CPC . A61B 17/32; A61B 17/320725; A61B 17/34; A61B 17/3478; A61B 18/06;
(Continued)

(56) References Cited

U.S. PATENT DOCUMENTS 5,370,677 A  12/1994 Rudie et al.
6,607,477 B1  8/2003 Longton et al.
(Continued)

FOREIGN PATENT DOCUMENTS

CN  101084038 A  12/2007
CN  101426551 A  5/2009
(Continued)

OTHER PUBLICATIONS

Davidson, et al. Interventional approaches for resistant hypertension. Curr Opin Nephrol Hypertens. 2012; 21(5):475-480.
(Continued)

*Primary Examiner* — Michael F Peffley
*Assistant Examiner* — Amanda L Zink
(74) *Attorney, Agent, or Firm* — Gardella Alciati

(57) ABSTRACT

Apparatus, systems, and methods for treating PKD by providing access to a patient's renal pelvis of a kidney to treat renal nerves embedded in tissue surrounding the renal pelvis. Access to the renal pelvis may be via the urinary tract or via minimally invasive incisions through the abdomen and kidney tissue. Treatment is effected by exchanging energy, typically delivering heat or extracting heat through a wall of the renal pelvis, or by delivering active substances to ablate a thin layer of tissue lining at least a portion of the renal pelvis to disrupt renal nerves within the tissue lining of the renal pelvis.

15 Claims, 35 Drawing Sheets

Related U.S. Application Data continuation of application No. 16/444,217, filed on Jun. 18, 2019, now Pat. No. 10,786,295, application No. 17/143,725 is a continuation-in-part of application No. 15/979,222, filed on May 14, 2018, now abandoned, said application No. 16/444,217 is a continuation of application No. 13/547,486, filed on Jul. 12, 2012, now Pat. No. 10,357,302.

(60) Provisional application No. 62/505,686, filed on May 12, 2017, provisional application No. 61/506,976, filed on Jul. 12, 2011.

(51) Int. Cl.
*A61B 18/08* (2006.01)
*A61B 18/18* (2006.01)
*A61M 25/10* (2013.01)
*A61N 7/02* (2006.01)
*A61B 18/04* (2006.01)

(52) U.S. Cl.
CPC ......... *A61B 18/1815* (2013.01); *A61M 25/10* (2013.01); *A61N 7/022* (2013.01); *A61B 2018/0016* (2013.01); *A61B 2018/0022* (2013.01); *A61B 2018/00267* (2013.01); *A61B 2018/00291* (2013.01); *A61B 2018/00404* (2013.01); *A61B 2018/00434* (2013.01); *A61B 2018/00511* (2013.01); *A61B 2018/044* (2013.01); *A61B 2018/046* (2013.01); *A61B 2018/143* (2013.01); *A61B 2018/1475* (2013.01)

(58) Field of Classification Search
CPC ...... A61B 18/1492; A61B 2017/22061; A61B 2017/320004; A61B 2017/320012; A61B 2017/32006; A61B 2018/00023; A61B 2018/0016; A61B 2018/0022; A61B 2018/00267; A61B 2018/00291; A61B 2018/00434; A61B 2018/00511; A61B 2018/00577; A61B 2018/00791; A61B 2018/00821; A61B 2018/00982; A61B 2018/044; A61B 2018/1417; A61B 2018/1435; A61B 2018/144
See application file for complete search history.

(56) References Cited

U.S. PATENT DOCUMENTS

| | | | |
|---|---|---|---|
| 7,653,438 | B2 | 1/2010 | Deem et al. |
| 7,717,948 | B2 | 5/2010 | Demarais et al. |
| 8,548,600 | B2 | 10/2013 | Deem et al. |
| 9,668,811 | B2 | 6/2017 | Sogard et al. |
| 10,357,302 | B2 | 7/2019 | Buelna et al. |
| 10,786,295 | B2 | 9/2020 | Buelna |
| 2002/0048310 | A1 | 4/2002 | Heuser |
| 2003/0216792 | A1 | 11/2003 | Levin et al. |
| 2006/0235474 | A1 | 10/2006 | Demarais |
| 2006/0276852 | A1 | 12/2006 | Demarais et al. |
| 2007/0129720 | A1 | 6/2007 | Demarais et al. |
| 2008/0086073 | A1 | 4/2008 | McDaniel |
| 2008/0228209 | A1 | 9/2008 | Demello et al. |
| 2009/0024195 | A1* | 1/2009 | Rezai .................. A61N 1/0558 607/116 |
| 2009/0192485 | A1 | 7/2009 | Heuser |
| 2010/0168731 | A1 | 7/2010 | Wu et al. |
| 2011/0015648 | A1 | 1/2011 | Alvarez et al. |
| 2011/0060324 | A1 | 3/2011 | Wu et al. |
| 2011/0104061 | A1 | 5/2011 | Seward et al. |
| 2011/0301662 | A1 | 12/2011 | Bar-Yoseph et al. |
| 2012/0109021 | A1 | 5/2012 | Hastings et al. |
| 2012/0123303 | A1 | 5/2012 | Sogard et al. |
| 2012/0130368 | A1 | 5/2012 | Jenson |
| 2013/0053732 | A1* | 2/2013 | Heuser .................. A61N 1/0551 601/2 |
| 2013/0178824 | A1* | 7/2013 | Buelna ............... A61B 18/1815 606/41 |
| 2014/0107639 | A1 | 4/2014 | Zhang et al. |
| 2015/0065783 | A1* | 3/2015 | Buelna .................. A61B 18/04 606/41 |
| 2018/0325587 | A1 | 11/2018 | Buelna et al. |
| 2019/0329042 | A1 | 10/2019 | DiLorenzo |
| 2020/0405368 | A1 | 12/2020 | Buelna |
| 2024/0099988 | A1 | 3/2024 | Buelna |
| 2024/0148423 | A1 | 5/2024 | Buelna |
| 2024/0189253 | A1 | 6/2024 | Buelna |

FOREIGN PATENT DOCUMENTS

| | | |
|---|---|---|
| CN | 101583323 A | 11/2009 |
| DE | 19701840 A1 | 11/1997 |
| EP | 2747830 A1 | 7/2014 |
| WO | WO-9103996 A1 | 4/1991 |
| WO | 2005/000130 | 1/2005 |
| WO | WO-2007078997 A2 | 7/2007 |
| WO | WO-2009097294 A1 | 8/2009 |
| WO | WO-2010067360 A2 | 6/2010 |
| WO | WO-2010067360 A3 | 9/2010 |
| WO | WO-2011046880 A2 | 4/2011 |
| WO | WO-2011053757 A1 | 5/2011 |
| WO | WO-2011082278 A1 | 7/2011 |
| WO | WO-2011112400 A1 | 9/2011 |
| WO | WO-2012170482 A1 | 12/2012 |
| WO | 2013010009 A1 | 1/2013 |
| WO | WO-2013028812 A1 | 2/2013 |
| WO | 2013134469 A1 | 9/2013 |

OTHER PUBLICATIONS

European search report and opinion dated Dec. 2, 2014 for EP Application No. 12811672.0.
"European search report dated Mar. 9, 2015 for EP Application No. 12825105.5.".
International search report and written opinion dated Oct. 2, 2012 for PCT/US2012/046511.
International search report and written opinion dated Jan. 17, 2013 for PCT/US2012/051950.
Notice of allowance dated Jun. 12, 2020 for U.S. Appl. No. 16/444,217.
"Office action dated Feb. 1, 2016 for U.S. Appl. No. 13/547,486.".
Office action dated Feb. 27, 2013 for U.S. Appl. No. 13/217,233.
Office action dated Apr. 22, 2015 for U.S. Appl. No. 13/217,233.
Office action dated May 6, 2015 for U.S. Appl. No. 13/547,486.
Office action dated Jun. 14, 2013 for U.S. Appl. No. 13/217,233.
Office Action dated Jun. 29, 2017 for U.S. Appl. No. 13/547,486.
Office action dated Sep. 9, 2020 for U.S. Appl. No. 15/979,222.
Office action dated Sep. 25, 2014 for U.S. Appl. No. 13/217,233.
Office Action dated Oct. 3, 2016 for U.S. Appl. No. 13/547,486.
Office action dated Dec. 26, 2014 for U.S. Appl. No. 13/547,486.
Office action dated Mar. 28, 2022 for U.S. Appl. No. 17/016,232.
1 Non-Final Office Action issued in U.S. Appl. No. 17/097,387 on Oct. 20, 2023, 14 pages.
Non-Final Office Action issued in U.S. Appl. No. 18/412,229 dated Apr. 9, 2024, 7 pages.
Non-Final Office Action issued in U.S. Appl. No. 18/412,240 dated Apr. 25, 2024, 17 pages.
U.S. Appl. No. 18/412,229, Notice of Allowance, issued Aug. 7, 2024.
U.S. Appl. No. 18/412,240, Notice of Allowance, issued Aug. 27, 2024.
U.S. Appl. No. 17/097,387, Notice of Allowance, issued Nov. 14, 2024.

* cited by examiner

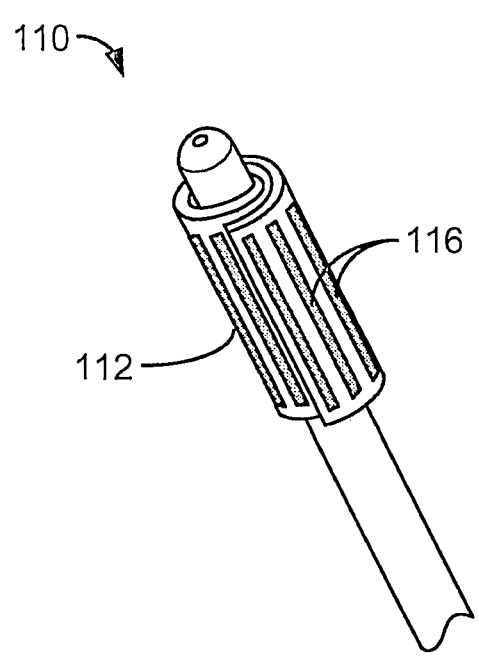
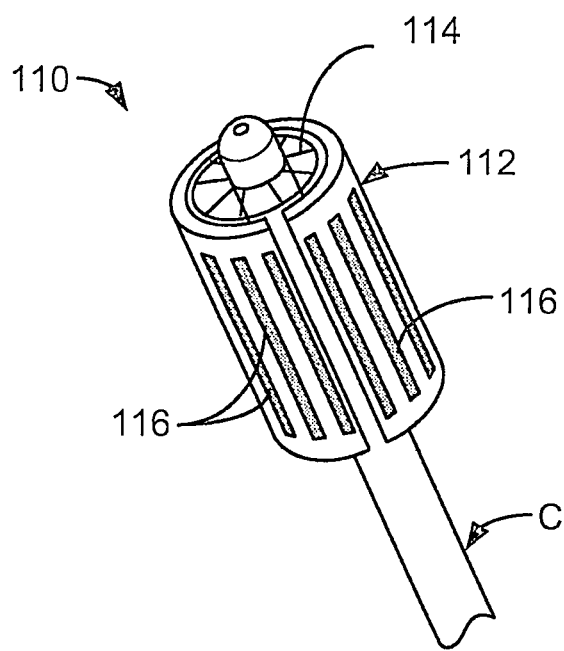
FIG. 9A
FIG. 9B

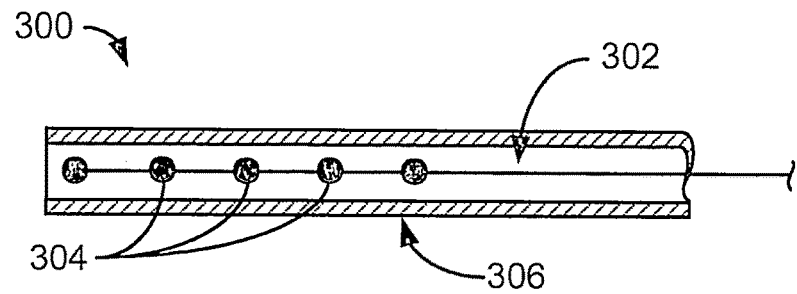
FIG. 27A
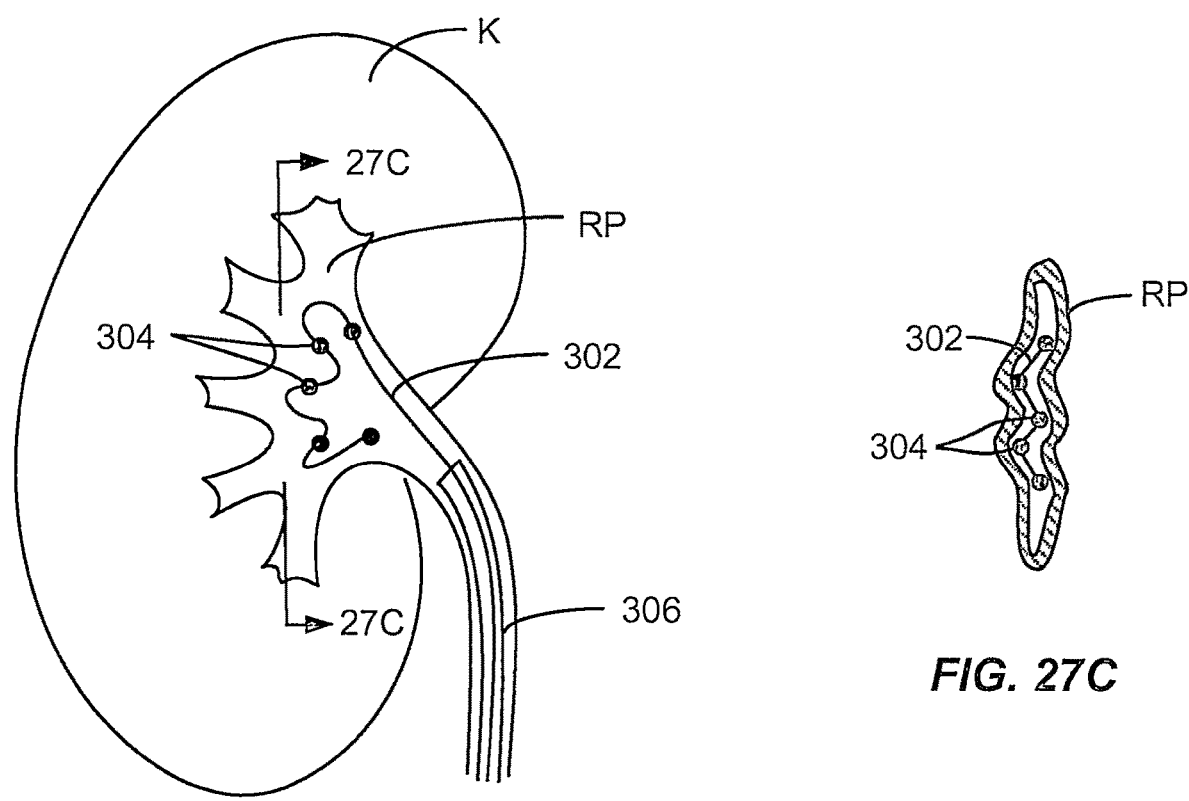
FIG. 27B
FIG. 27C

METHODS AND DEVICES FOR TREATING POLYCYSTIC KIDNEY DISEASE AND ITS SYMPTOMS

CROSS-REFERENCE TO RELATED APPLICATIONS

This application is a continuation-in-part of U.S. patent application Ser. No. 15/979,222, filed May 14, 2018, now abandoned, which claims the benefit of provisional patent application 62/505,686, filed May 12, 2017, the entire contents of which are incorporated herein by reference; this application is also a continuation-in-part of U.S. patent application Ser. No. 17/016,232, filed Sep. 9, 2020, now abandoned; which is a continuation of U.S. patent application Ser. No. 16/444,217, filed Jun. 18, 2019, now U.S. Pat. No. 10,786,295, which is a continuation of U.S. patent application Ser. No. 13/547,486, filed Jul. 12, 2012, now U.S. Pat. No. 10,357,302, which claims the benefit of U.S. Provisional No. 61/506,976, filed Jul. 12, 2011, the entire contents of which are incorporated herein by reference.

BACKGROUND OF THE INVENTION

1. Field of the Invention

The present invention relates generally to medical devices, systems, apparatus, and methods for modifying nerve function and treating disease. More particularly, the present invention relates to methods and apparatus for treating polycystic kidney disease.

Polycystic kidney disease or PKD is characterized by multiple fluid filled cysts on one or both kidneys which potentially can cause excessive enlargement of both kidneys. Autosomal dominant PKD (ADPKD) is the most prevalent form and constitutes about 85% of all polycystic kidney disease. ADPKD is a genetically inherited disease which affects up to 600,000 people in the US alone. These patients typically progress to end stage renal disease by the time they are in their 50's. Two of the most problematic clinical manifestations of PKD are hypertension and pain. Pain generally located in the flank or lower back. Both of these problems are directly related to increased afferent nerve activity in the kidney. The afferent nerves are generally divided into two categories, mechanoreceptors and chemoreceptors. Mechanoreceptors are sensory nerves that respond to stretch and chemoreceptors that respond to chemical changes from chemicals such as adenosine, norepinephirine and dopamine.

Heretofore, PKD the multiple enlarged cysts activate the afferent sensory nerves which originate primarily in the collecting system or renal pelvis. This overactive nerve response sends a signal travels to the brain via the spinal cord which can result in pain and hypertension. Treatment of pain is conservatively managed by non-steroidal anti-inflammatory drugs (NSAIDS) or acetaminophen. With diseased kidneys, it is not recommended to use NSAIDS as they have a toxic affect and are known to compromise kidney filtration rate (GFR). Surgical interventions such as laparoscopic and thoracoscopic denervation, cyst aspiration and kidney decortication have had some success but they are all invasive, and repeat surgery is often necessary as the cysts grow back. Laparoscopic denervation though effective, has an average operating time of 2 to 3 hours and hospitalization stay of 2-3 days.

More recently, devices and procedures that percutaneously access the lumen of the renal artery and apply RF ablative energy, ultrasound energy, microwave energy and alcohol through the artery wall into the surrounding nerves that envelop the artery and traverse down the artery to the hilum of the kidney. This procedure, percutaneous renal denervation, RDN destroys the nerves and interrupts the nerve signal travelling to the kidney. These sympathetic nerve bundles are comprised of approximately 80-90% efferent nerves travelling to the kidney and 10-20% afferent sensory nerves travelling the opposite direction to the spinal cord and then to the brain. Early studies have shown success in relieving pain in these patients as well as a reduction of blood pressure. Accessing the renal arteries are problematic with many of these patients as diseased kidneys generally have diseased arteries and often arterial stenosis. The procedure also depends on fluoroscopic imaging with systemic contrast for placement of the catheter and confirmation of post treatment patent arteries. Systemic contrast is toxic to diseased kidneys and should not be used on most patients.

For these reasons, it would be desirable to provide alternative protocols and apparatus for treating polycystic disease via alternative and less problematic routes and modes of therapy. It would be further desirable if such routes and modes of therapy could be performed minimally invasively, would present a reduced risk of injury and trauma to the patient, were economical, and could be performed using simplified and scalable methods. At least some of these objectives will be met by the inventions described herein below.

2. Description of the Background Art

U.S. Patent Publication Nos. 20011/0301662; 2013/0053732; and 2013/0178824 and WO2012/170482 describe apparatus, systems, and methods for ablating or modulating nerves or tissue via the renal pelvis. U.S. Patent Publication No. 2011/0060324 describes apparatus, systems, and methods for performing thermally-induced renal neuromodulation by intravascular access. U.S. Patent Publication No. 2011/0104061 describes apparatus, systems, and methods for active agents to the renal arteries for achieving renal denervation. Published PCT Application WO2010/067360 describes methods and apparatus for modifying blood pressure and kidney function via stimulation of the urinary tract by stimulating the renal nerves. U.S. Pat. No. 8,548,600 describes an intravascular electrode device for delivering energy which may include cylindrical electrodes on a helical deployment wire.

BRIEF SUMMARY OF THE INVENTION

Generally, the present invention provides methods for inhibiting or modulating the function of renal nerves in a patient's kidney. The purpose of the inhibition or modulation could be for treating systemic hypertension, chronic kidney disease, chronic heart disease, sleep apnea, chronic pain, polycystic kidney disease, insulin resistance, obesity, benign prostate hyperplasia, (BPH), or for other purposes. The method is carried out by introducing an effector into an interior of the kidney and exchanging energy and/or delivering active substances from the interior of the kidney through a wall of the renal pelvis to the renal nerves within the pelvic wall as well as surrounding the renal blood vessels within the kidney or UPJ. In many embodiments, the methods will rely on delivering energy to raise the temperature of the renal pelvis and the tissue bed surrounding the blood vessels to a temperature within a target range sufficient to inhibit or destroy nerve function (denervation) typically being in the range from 45° C. to 80° C., usually in the range from 45° C. to 60° C., typically for a time in the range from 3 sec. to 4 minutes, usually from 1 minute to 2 minutes. In such cases, the energy delivery will preferably be directed or limited so that tissue beyond that surrounding the renal pelvis, such as other renal structures including the papillae, the pyramids, and the like, is maintained below a temperature which would adversely affect the tissue function, typically below 45° C. A number of particular methods and devices for delivering energy to raise the tissue temperature are described in more detail below. In other embodiments, the energy exchange may comprise extracting energy from the tissue bed surrounding the blood vessels to cool said tissue bed to the temperature in the range from −10° C. to −100° C., typically from −50° C. to −100° C. Such cooling of the tissue will typically be carried out for a time period in the range from 3 sec. to 4 minutes, usually from 1 minute to 4 minutes. As with heating, the present invention will also limit the cooling of tissue surrounding the renal pelvis to a temperature which will not adversely affect tissue function, typically above −10° C.

More specifically the Methods of the present invention are intended for treating patients diagnosed with PKD, where said methods comprise accessing and disrupting a patient's afferent nerves at their origin within the walls of the renal pelvis. This is accomplished by advancing or otherwise directing a treatment catheter transurethrally and transureterally into the kidney, typically at its center. The catheter has an electrode array on its distal end which allows contact with the walls of the renal pelvis once the catheter is in position. Monopolar radiofrequency energy is then directed from a low power <50 w generator through the catheter and electrodes into the renal pelvic tissue. A controller on the generator limits the treatment duration, monitors impedance between the electrodes and the grounding pad located on the patient and monitors temperature of the electrode/tissue interface. The treatment time is generally between 1 min and 3 minutes, temperature 50-70° C. The catheter is placed over a guidewire which has been placed under endoscopic vision to the treatment site in the renal pelvis. A renal pylogram confirms proper placement in the treatment area. An alternative method is to use a sheath in place of the guidewire. A 16F sheath will allow the treatment catheter and ureteroscope to pass through the ureter and facilitate placement and treatment to be completed under direct vision without the need for a pylogram or fluoroscopic imaging. Upon completion of the treatment, a temporary ureteral stent is placed to maintain patency. The treatment results are a disruption of the afferent nerves by ablation within the wall of the renal pelvis. Monopolar RF and electrode design allows for directed controlled disruption of the nerves which traverse the renal pelvic tissue between the muscle layers and around the vessels within the wall of the pelvis. Scattered afferent nerves are also embedded in the urothelium lining which is in direct contact with the treatment electrodes. The renal pelvis is generally 1-2 mm thick and the urothelium less than 0.25 mm.

Disruption of these nerves, which form a dense network in the treatment area, disrupts the signal to the spinal column and then the brain that controls localized kidney pain from the mechanoreceptors, chemoreceptors and sympathetic tone which regulates blood pressure and hypertension. Hypertension is common in the PKD patient group and managing this symptom can improve blood flow to the kidney which will result in lower blood pressure, improved filtration (GFR) and reduce cyst size and proliferation.

The methods can use the devices described in US patent publication US2013/0053732 titled "Devices and Methods for Treating Hypertension with Energy" and PCT publication PCT/US12/46511 titled "Renal Nerve Denervation via the Renal Pelvis," the full disclosures of which are incorporated herein by reference, as described in detail hereinbelow.

Such devices are particularly advantageous as they may be easily positioned by a steerable or other sheath to position the balls or other point electrodes in the center of the renal pelvis, or any other desired location. Since the sheath and the device are not locked together, the device can be rotated relative to the sheath. This allows the sheath to maintain its curve while the helix is rotated for better positioning.

The diameter of the balls is significantly larger than an outside diameter (OD) of the insulation on the supporting wire. An exemplary design has a ratio of 3.4:1 (0.078 in to 0.023 in) which allows the tissue to conform around the electrodes, ensuring that the electrodes will have a large contact surface area and excellent tissue contact. The geometry also helps guarantee a larger electrode-to tissue contact force. The larger contact surface area, improved electrode/tissue contact, and larger electrode/tissue contact force are all desirable for safe, proper, and efficient energy delivery and lesion geometry. The helical/spiral shape of the device will cause the balls to press against the walls of the renal pelvis. The spacing of the balls and the helical shape creates discreet lesions in the renal pelvis on different tissue planes. This ensures that there is enough healthy tissue left intact so that the pelvis and ureter do not stricture significantly.

In a first aspect of the present invention, a method for inhibiting or modulating the function of renal nerves in a patient's kidney comprises introducing an effector into an interior of the kidney or an upper region of an adjacent ureter. Energy is exchanged or active substances delivered from effector in the interior of the kidney to ablate a layer of tissue lining at least a portion of the renal pelvis to disrupt renal nerves within the tissue lining and optionally muscle layers of the renal pelvis. The layer typically includes the urothelium and the lamina propria. While the ablation occurs primarily within the urothelium and the lamina propria, in some instances ablation can extends into connective tissue and a vascular layer that surrounds the lamina propria and muscle layers.

The depth of ablation is controlled to achieve a desired ablation with minimal damage to the kidney and kidney function. Typically the ablation extends to a depth in the range from 0.1 mm to 2 mm, usually from 0.2 mm to 1.5 mm, and often from 0.5 mm to 1.2 mm. Such ablation depth can be achieved by delivering electrical energy, typically radiofrequency current, over a continuous region of the renal pelvis at a power in the range from 1 W to 200 W.

Introducing the effector may comprise advancing the effector through the urinary tract to the renal pelvis. For example, the effector may be disposed on a urinary catheter, and the urinary catheter may be advanced through the urethra, bladder, and ureter to reach the renal pelvis. Alternatively, introducing the effector may comprise advancing the effector percutaneously to the renal pelvis.

Energy may be delivered in a variety of ways. For example, the effector may comprise electrodes and the energy may comprise radiofrequency energy which is delivered to heat the wall of the renal pelvis and renal nerves embedded in the tissue bed surrounding the renal blood vessels. Alternatively, the effector may comprise an antenna and the energy may comprise microwave energy which is delivered to heat the wall of the renal pelvis and renal nerves embedded in the tissue bed surrounding the renal blood vessels. Further alternatively, the effector may comprise an ultrasound transducer and the energy may comprise ultrasound energy which is delivered to heat the wall of the renal pelvis and renal nerves embedded in the tissue bed surrounding the renal blood vessels. As a specific example of ultrasound energy, the ultrasound transducer may comprise a high intensity focused ultrasound transducer array. Other energy effectors may comprise a convective heat source which delivers heat through the renal pelvis to heat the wall of the renal pelvis and renal nerves embedded in the tissue bed surrounding the renal blood vessels. A specific example of a convective heat source would deliver a heated fluid within an inflated chamber deployed within the renal pelvis. Conversely, the effector may comprises a convective cooling source where heat is extracted through the renal pelvis to cool the wall of the renal pelvis and renal nerves embedded in the tissue bed surrounding the renal blood vessels. An exemplary convective cooling source comprises a cooled fluid deployed within an inflated chamber within the renal pelvis. Still other effectors may comprise a radiation-emitting source, either a radioisotope or an X-ray or other electronic radiation. Other examples include effectors having tissue-penetrating electrodes which are penetrated into a wall of the renal pelvis while energy is delivered to the wall through the electrodes. In yet other examples, the energy exchanged is mechanical energy such as abrasion or cutting.

In a second aspect of the present invention, an electrode structure comprises a self-expanding deployment wire having a distal region configured to expand into and engage a wall of a renal pelvis. A plurality of rounded electrode members is distributed over said distal region where each rounded electrode member has a surface which extends radially outwardly beyond the surface of the adjacent wire.

The distal region of the deployment wire typically has a three-dimensional expanded geometry, such as a helical or spiral distal geometry or may have a two-dimensional geometry, such as a looped distal end. Even lop structures, hover, may have secondary structures, such a bending or local coiling, to impart a third dimension to a planar geometry. Typically, at least the distal region of the deployment wire is electrically insulated over its surface between the rounded electrodes. The diameter of the rounded electrode structure may be from two-fold to six fold greater than that of the deployment wire, and exemplary electrode will have a deployment wire diameter in the range from 0.1 mm to 7 mm and a rounded electrode member diameter in the range from 0.25 mm to 2.5 mm. In specific embodiments, the rounded electrodes are ball electrodes.

The electrode structures are frequently incorporated in an electrode deployment assembly which comprises the electrode structure as above with a delivery tube having a central, passage. The electrode structure is reciprocatably received the central passage of the delivery, wherein the distal region of the deployment wire is radially constrained when present in the passage and radially expanded when advanced distally out of the passage. The electrode structure is usually free to rotate in the passage of the delivery tube.

In a third aspect of the present invention, a method for delivering energy to a renal pelvis comprises introducing a wire into the ureter adjacent to or within the renal pelvis. The wire has a pre-shaped distal region configured to conform to the renal pelvis. The distal portion of the wire is advanced into the renal pelvis, wherein the distal portion is radially constrained while being advanced, and the distal region of the wire is released from constraint within the renal pelvis to engage tissue over a wall of the renal pelvis. Energy is applied to the wall of the renal pelvis through a plurality of electrodes on the wire, wherein the electrodes have rounded surfaces (typically being ball electrodes) which extend beyond the surface of the adjacent wire and which embed into the renal pelvis wall.

In exemplary embodiments, a vacuum may be applied within the renal pelvis while applying energy to draw the walls of the renal pelvis against the rounded electrodes. The pre-shaped distal region of the wire may have a helical, spiral, looped or other two-dimensional or three-dimensional distal geometry. At least the pre-shaped distal region of the wire will usually be electrically insulated over its surface between the electrodes, and the diameter of the electrodes will usually be from two-fold to six fold greater than that of the wire. In specific embodiments, the wire has a diameter in the range set forth above and the electrodes have a diameter in the range set forth above. In an exemplary protocol, the distal portion of the wire is advanced into the renal pelvis from a central passage of a delivery tube which had been positioned in the renal pelvis, wherein the distal region is radially constrained when present in the passage and radially expanded when advanced distally out of the passage.

BRIEF DESCRIPTION OF THE DRAWINGS

The novel features of the invention are set forth with particularity in the appended claims. A better understanding of the features and advantages of the present invention will be obtained by reference to the following drawings and detailed written description that set forth illustrative embodiments in which the principles of the invention are utilized.

FIGS. 9A and 9B illustrate an alternative device configured to ablate one or more tissue layers of the renal pelvic wall.

FIGS. 27A-27C show ball electrodes attached to superelastic alloy wire inside a catheter tube and subsequently deployed in a renal pelvis.

DETAILED DESCRIPTION OF THE INVENTION

Figure 1:
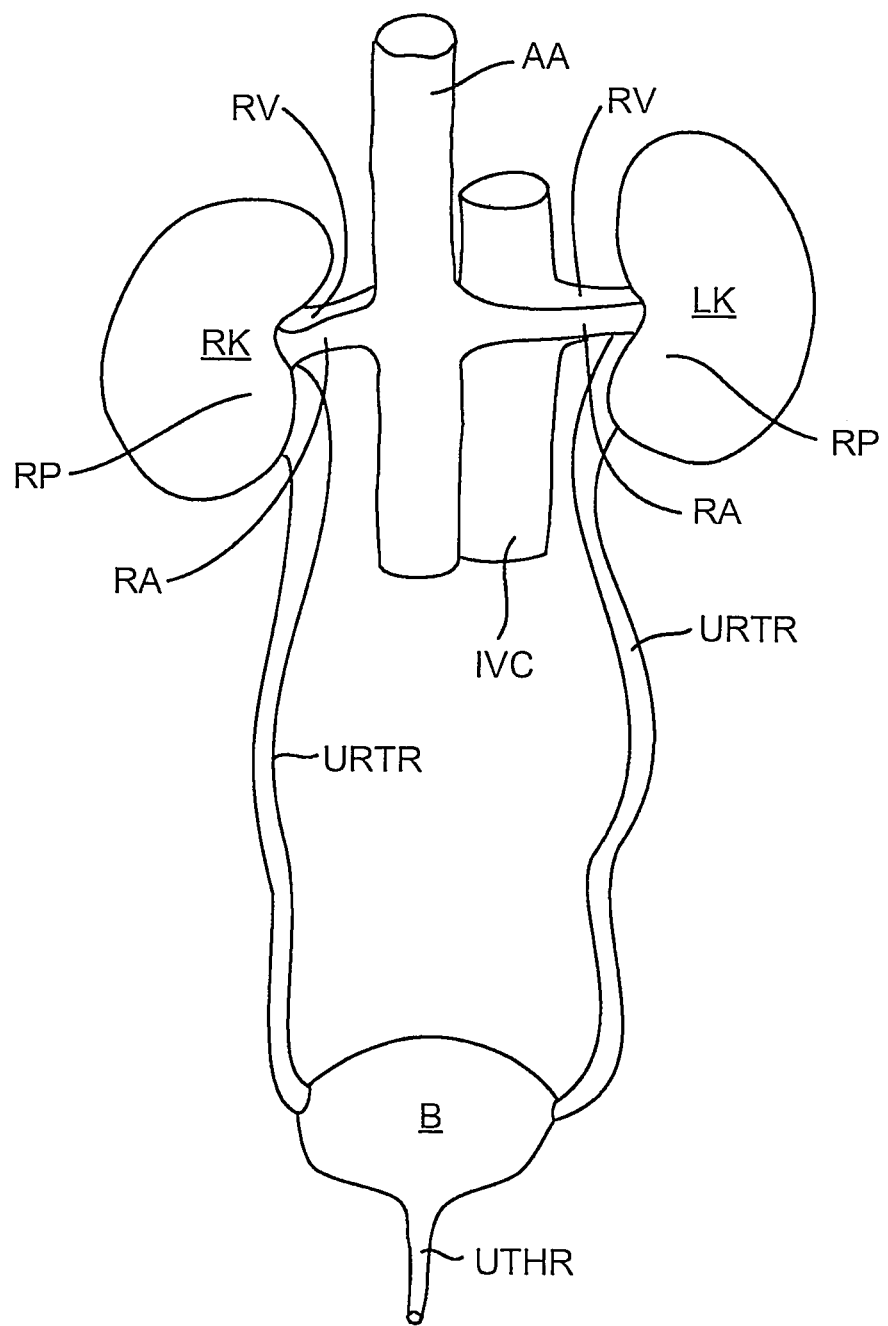
FIG. 1 is a diagrammatic illustration of a patient's urinary system.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

A patient's urinary tract is diagrammatically illustrated in FIG. 1. The urinary tract includes the bladder B, which receives urine from the right and left kidneys RK and LK and drains the urine through the urethra UTHR. The kidneys each receive oxygenated blood through the renal artery RA from the abdominal aorta AA and blood from the kidneys is returned through the renal vein RV to the inferior vena cava IVC. Of particular interest to the present invention, the urine which is processed in the kidney is received in an interior cavity of each kidney referred to as the renal pelvis RP which acts as a funnel and delivers the urine into the top of the ureter URTR. The methods and protocols of the present invention will be performed within the interior of the renal pelvis RP in order to treat the renal nerves within the walls of the renal pelvis as well as the nerves surrounding the renal arteries within the adventitia and adipose tissue and to a lesser extent surrounding the renal veins which branch from the main renal artery and renal vein within the tissue of the kidney.

Figure 2A:
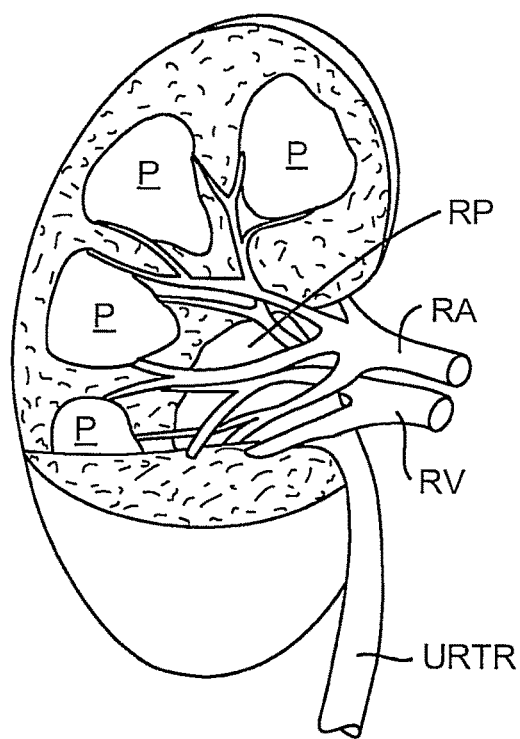
FIGS. 2A and 2B are partially broken-away illustrations of a patient's kidney showing the renal pelvis and other structures.
Figure 2B:
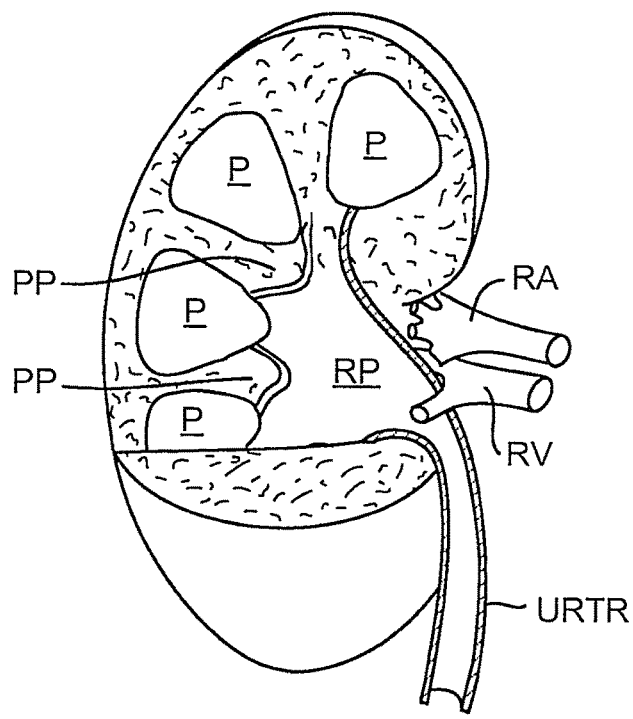
Figure 3:
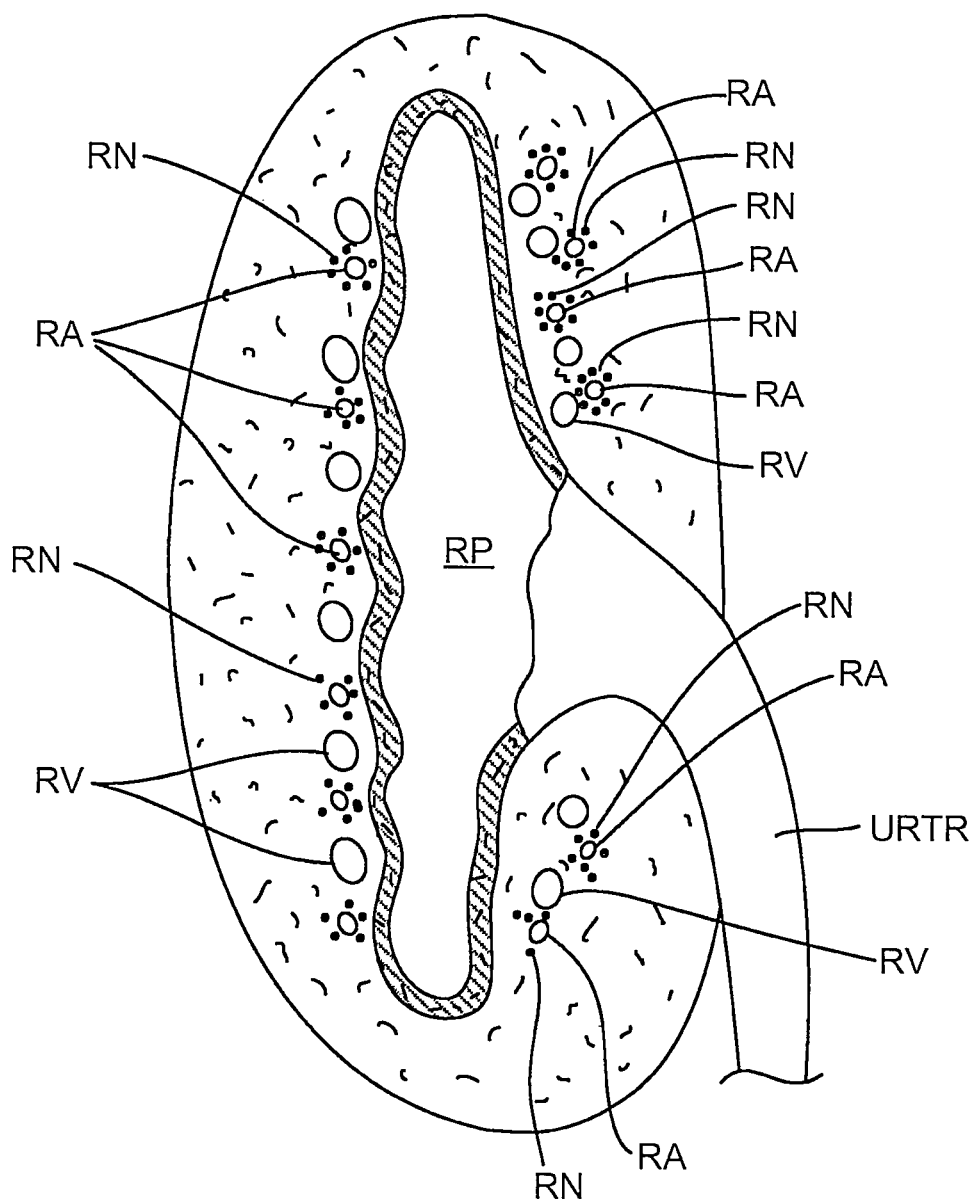
FIG. 3 is a cross-sectional view of the patient's kidney taken along line 3-3 of FIG. 2A.
Figure 3A:
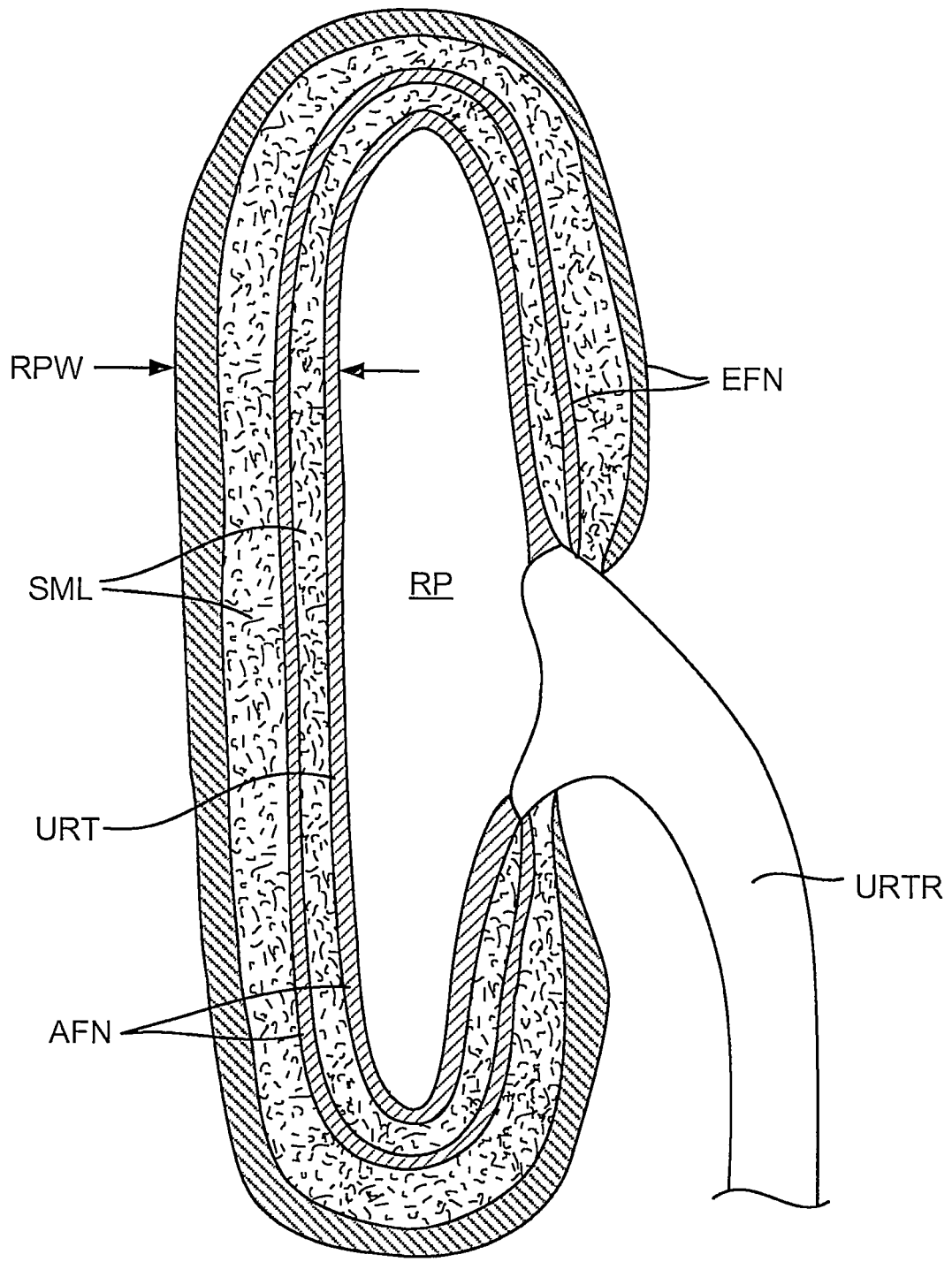
FIG. 3A shows the structure and location of renal nerves within the muscle layers, endothelium and submucosa of the renal pelvis. The afferent nerves originate and are mostly contained within the wall of the renal pelvis. They have a direct effect on the efferent sympathetic nerves and are responsible for sympathetic muscle tone and vasoconstriction.

Referring now to FIGS. 2A and 2B, the right kidney RK is shown in section to expose the renal pelvis RP and other internal structures of the kidney. As shown in FIG. 2A, the renal pelvis is a funnel-shaped extension of the upper and of the ureter URTR and is surrounded by the branching portions of the renal artery RA and the renal vein RV, both of which branching structures extend into the body of the kidney and surround the pyramids P and other structures, including the papillae PP. The branching structures of the renal artery RA and renal vein RV as well as the anterior wall of the renal pelvis are removed in FIG. 2B to show the interior of the renal pelvis which is the target location for the therapies of the present invention As further shown in FIG. 3 which is a cross-sectional view taken along line 3-3 of FIG. 2A, the renal nerves RN surround the renal blood vessels, particularly the renal arteries RA, extending adjacent to and surrounding the outer wall of the renal pelvis RP in a tissue bed surrounding the renal pelvis. As shown in FIG. 3A, the renal nerves follow the arteries and then divide. A portion of the divided nerves enter the renal pelvic wall RPW where they intertwine with the afferent nerves AFN that are located within the smooth muscle layers, endothelium and submucosa SML of the renal pelvis. The afferent nerves AFN originate and are mostly contained within an interior wall of the renal pelvis adjacent to the urothelium URT. The afferent nerves have a direct effect on the efferent sympathetic nerves EFN (which are generally located nearer the exterior surface of the renal pelvis wall RPW than are the afferent sensory nerves AFN) and are responsible for sympathetic muscle tone and vasoconstriction. It is the renal nerves shown in FIGS. 3 and 3A, and in particular the sensory afferent nerves AFN, which are typically but not exclusively the target structures to be treated by the methods and apparatus of the present invention.

Figure 4A:
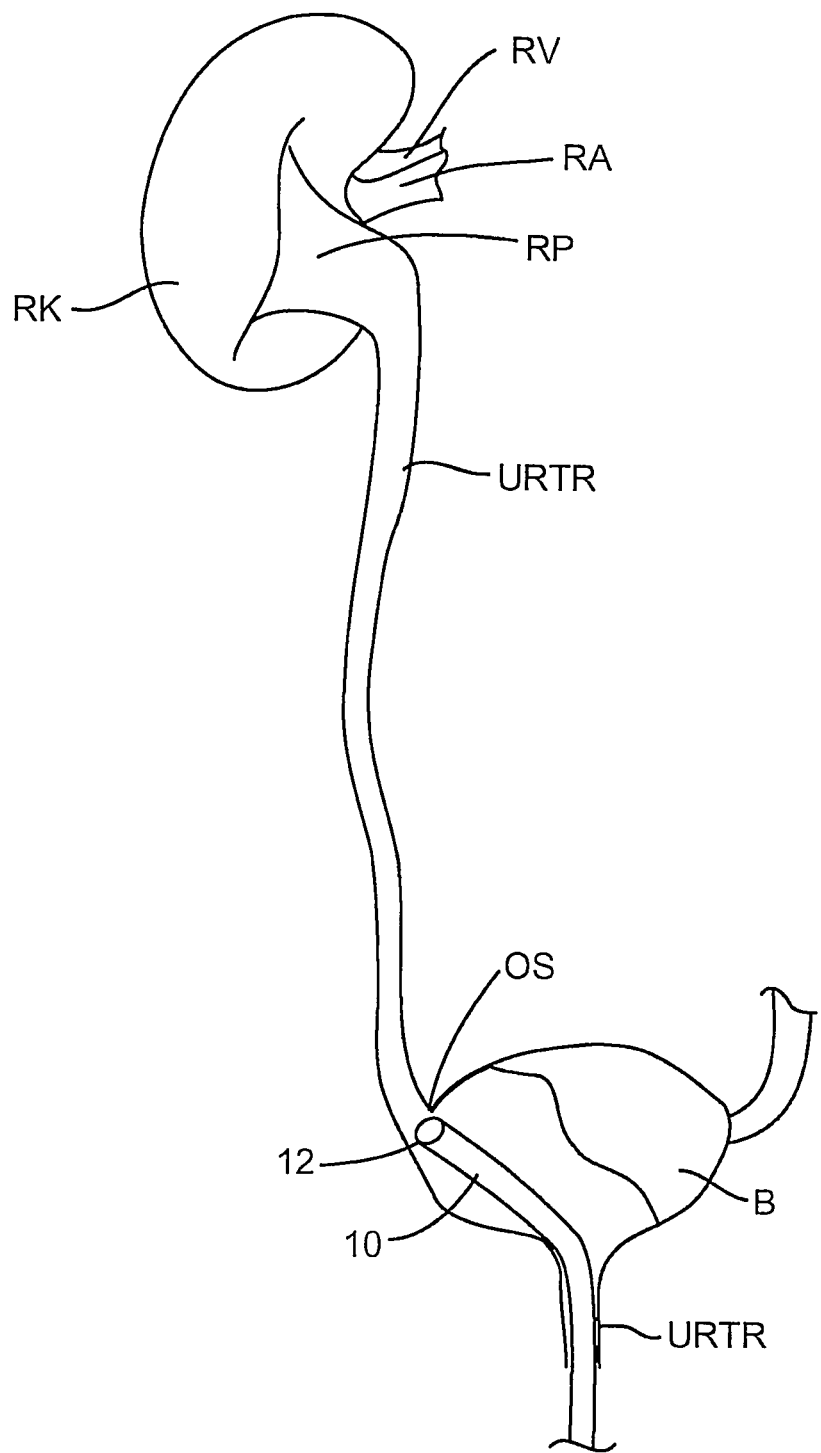
FIGS. 4A through 4C illustrate access and treatment of a patient's renal pelvis according to the principles of the present invention.
Figure 4B:
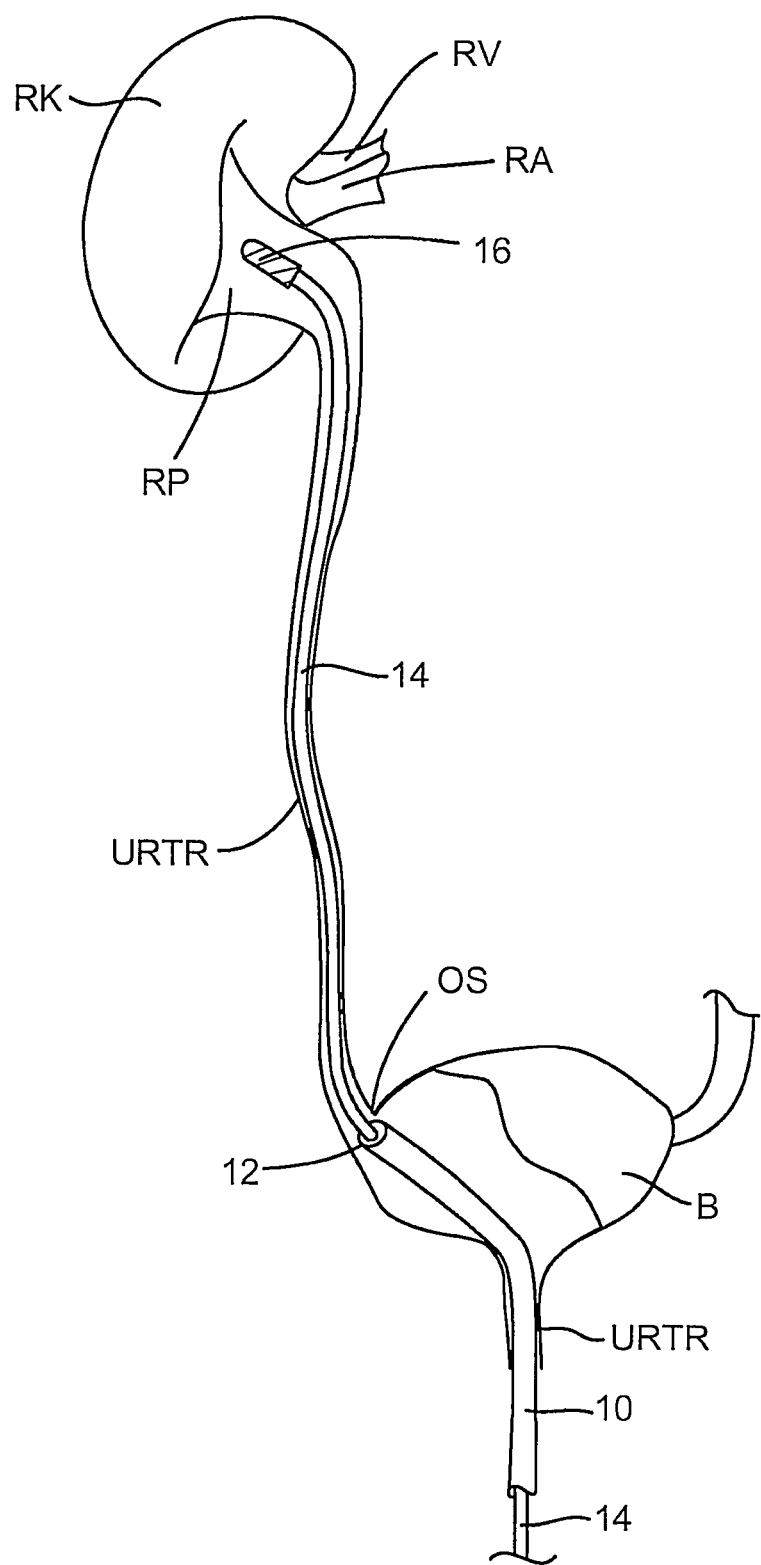
Figure 4C:
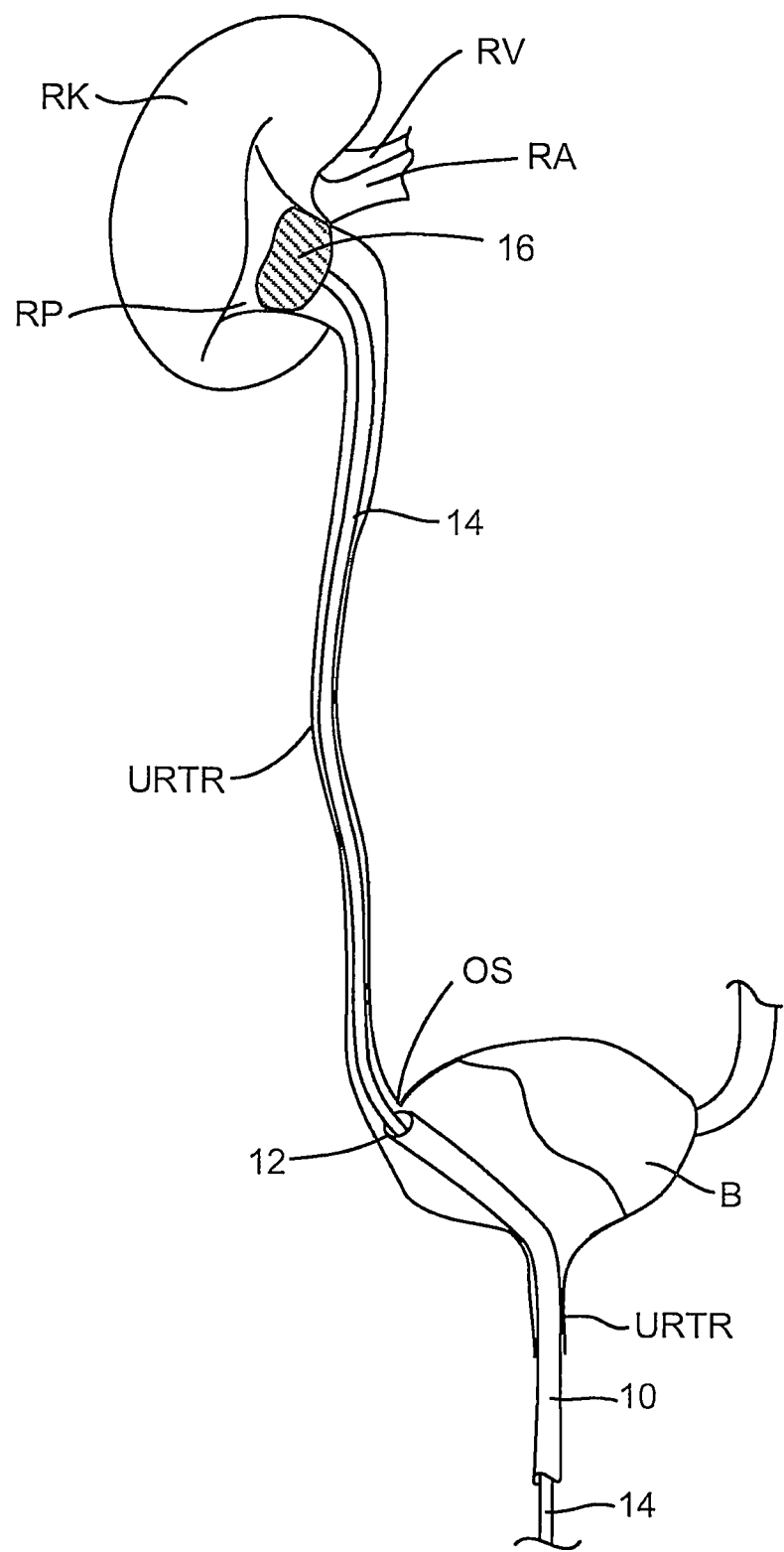

Referring now to FIGS. 4A through 4C, a first exemplary protocol for accessing and treating the renal nerves in the kidney will be described. Initially, a guide or other tubular catheter 10 is advanced through the urethra UTHR to position a distal port 12 adjacent the os OS at the lower end of the uereter URTR.

As shown in FIG. 4B, a treatment catheter 14 is then advanced through the guide catheter 1 (optionally over a guidewire), out of port 12, and into a lumen of the ureter URTR. An effector 16 at the distal end of the treatment catheter 14 is advanced into the renal pelvis RP, optionally under fluoroscopic and/or ultrasound guidance in a conventional manner.

Once in the renal pelvis RP, the effector 16 will be deployed in order to treat the renal nerves in accordance with the principles of the present invention. For example, the effector may comprise an expandable structure which is mechanically expanded or inflated within the renal pelvis to engage the interior walls of the pelvis as shown FIG. 4C. Any one of a variety of energy exchange devices or substance delivery devices may then be employed to exchange energy or deliver the substances through the wall of the renal pelvis to treat the nerves embedded within the walls.

Figure 5:
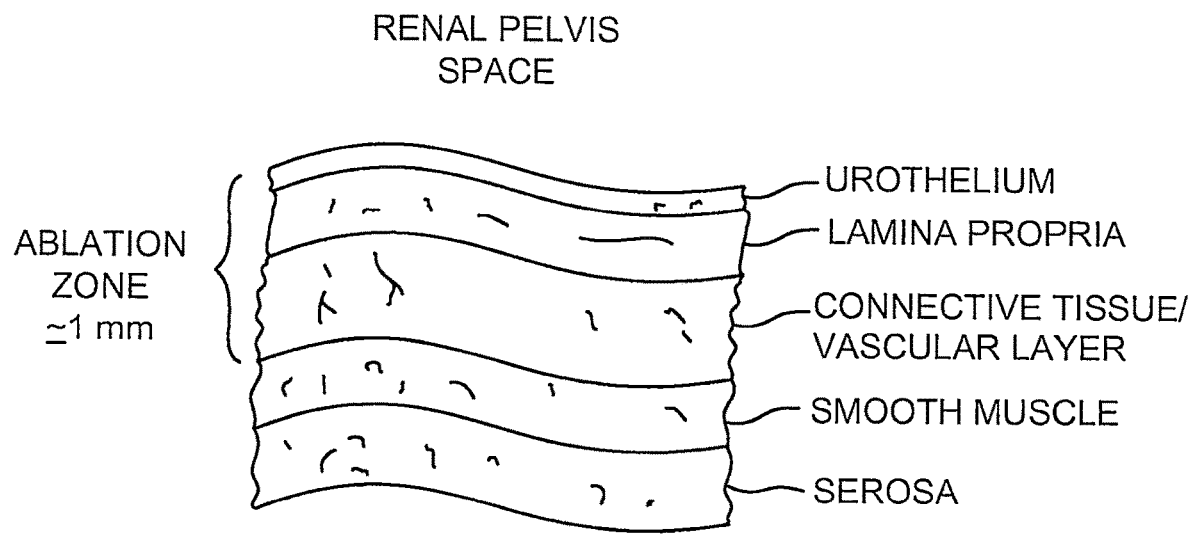
FIG. 5 illustrates the tissue layers of the renal pelvic wall.

In some instances, devices and methods will be configured to ablate a thin layer of tissue which lines the renal pelvic. The renal pelvic wall consists of multiple tissue layers as shown in FIG. 5. Afferent and efferent nerves exist through the layers, and there is a high concentration of afferent nerves close to the surface (e.g. within the urothelium, lamina propria, and extending into a first muscle layer). Together, the urothelium and lamina propria layers will be referred to as the "tissue lining the renal pelvis." The inventors herein have determined that moderate to extensive damage to the muscle layers may cause stenosis of the renal pelvis, which is of course undesirable. The inventors herein have further determined that the creation of very shallow lesions on the interior wall of the renal pelvis will target the surface afferent nerves (thus achieving renal denervation), while leaving the surrounding tissue (muscle, blood vessels, etc.) intact.

This result can be achieved with any number of devices, including those described in commonly owned U.S. Patent Publication 2013/0178824, the full disclosure of which is incorporated herein by reference, as well as a number of other devices described below. Energy or substance delivery through the devices must be carefully controlled to achieve the desired effect. Exemplary protocols will apply RF energy at high power (e.g. 50-200 Watts) and short application times (e.g. 0.1-15 seconds). In other instances, however, it may be possible to achieve similar ablation using low power (e.g. 1-50 Watts) and longer times (e.g. 60-300 seconds). Lesion depth should be between 0.1 mm and 2 mm, usually between 0.2 mm and 1.5 mm, and often between 0.5 mm and 1.2 mm. FIG. 5 shows the ablation zone depth.

Surface lesions having the desired depths can be created by regulating temperature, time, power, and/or impedance. More specifically, the lesion depth can be controlled by applying a specified power until specified impedance is reached. Alternatively, the lesion depth can be controlled by maintaining a specified temperature for a specified length of time. Under any control algorithm, time, power, temperature, and impedance can be monitored for safety limits.

Figure 6:
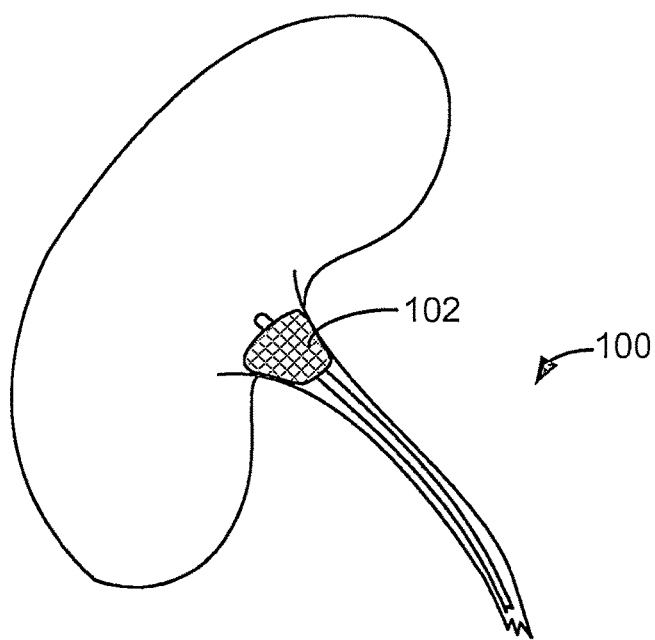
FIG. 6 illustrates a device configured to ablate one or more tissue layers of the renal pelvic wall.
Figure 7:
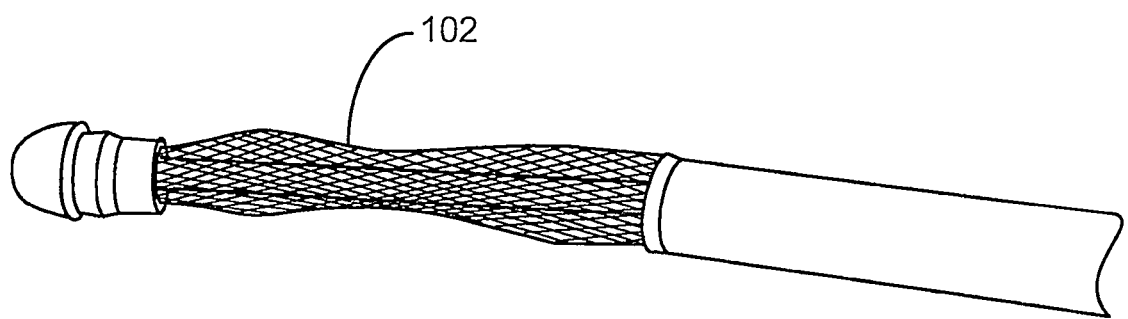
FIGS. 7 and 8 show a mesh electrode of the device of FIG. 6 on its collapsed and expanded configurations, respectively.
Figure 8:
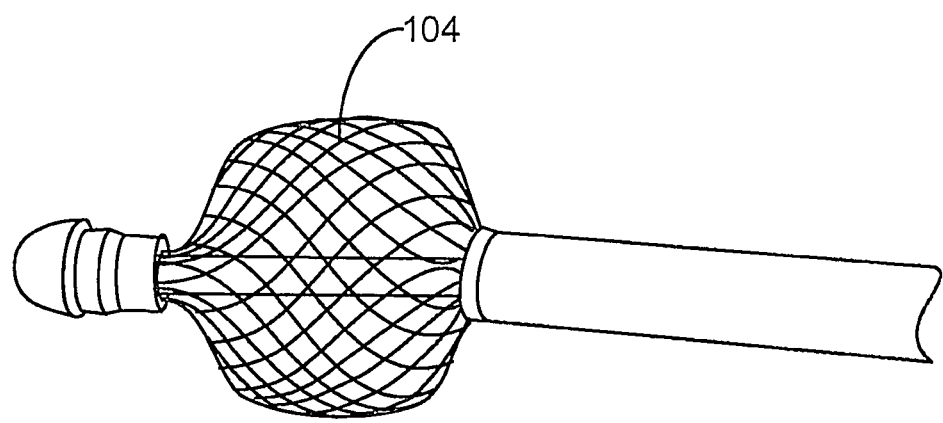

An exemplary device 100 for delivering RF power to the renal pelvis is shown in FIGS. 6-8. The device includes tubular Nitinol® mesh electrode 102 that is expanded at the target site in the renal pelvis, as shown in FIG. 6. Monopolar energy is delivered through all wires of the expanded mesh to create the desired lesion. The diameter of the device is typically 7 Fr-11 Fr in the collapsed state (FIG. 7). The diameter of the mesh is typically 8 mm-20 mm in the expanded state (FIG. 8). The length of the mesh electrode is usually 8-20 mm in the expanded state. Use of a mesh electrode is desirable as it readily conforms to the shape of the renal pelvis.

In other embodiments, the electrodes on the delivery catheter may comprise balloons with conductors formed over their external surfaces, e.g. by conductive inks or conductive wire.

In a further exemplary device 110, an expandable flex circuit 112 can be located over a balloon 114 or other inflatable/radially expandable structure, as shown in FIGS. 9A and 9B. In this design, the flex circuit is initially rolled over the balloon (FIG. 9A), and balloon is inflated to expand and unroll the flex circuit (FIG. 9B) so that electrode(s) 116 and optionally thermocouple(s) (not shown) formed on the exterior surface of the flex circuit contact the renal pelvic wall tissue when the flex circuit is expanded. As an alternative to a rolled-up flex circuit, the flex circuit could have other expandable geometries, such as pleated, patterned (similar to an arterial stent), or the like, so that it is able to expand from a low diameter delivery configuration to a larger diameter deployed configuration. Flex circuit dimensions are typically 7 Fr-11 Fr in the collapsed state (FIG. 9A) and 8-20 mm diameter and 8-20 mm length in the expanded state (FIG. 9B). These designs can be monopolar or bipolar, the latter being useful in limiting surface lesion depth.

Another approach to creating effective renal denervation lesions without damaging renal pelvic function is to create deeper lesions only in specific areas. This will leave healthy tissue intact, avoiding strictures in the renal pelvis. Multiple devices are disclosed below to achieve this effect.

Figure 10A:
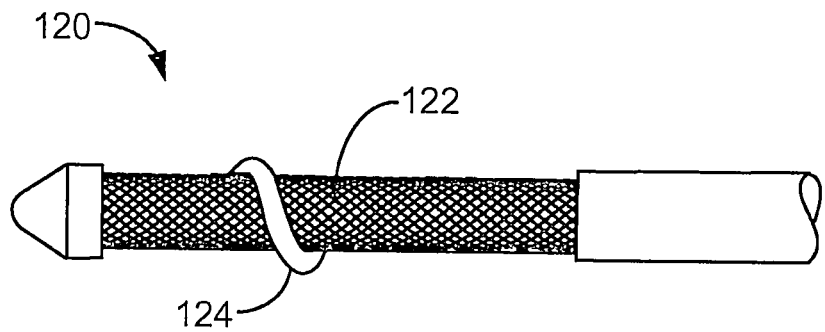
FIGS. 10A-10C illustrate devices configured to create deeper lesions in the renal pelvic wall.
Figure 10B:
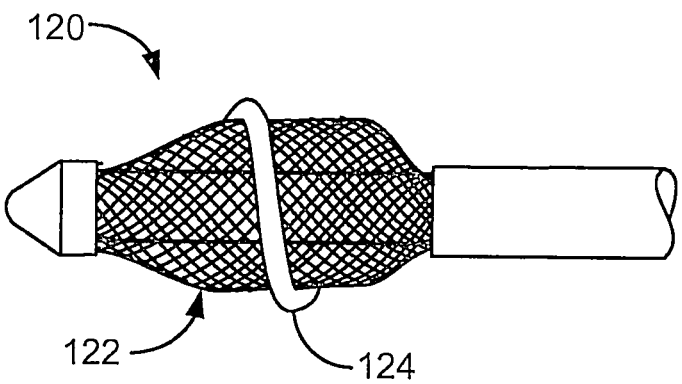
Figure 10C:
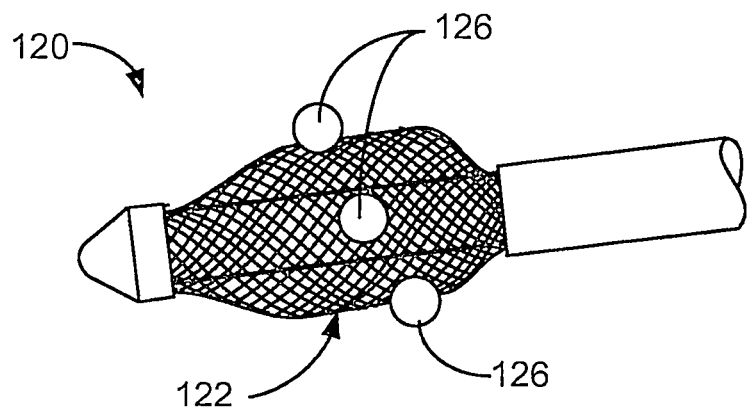

As shown in FIGS. 10A-10C, a device 120 carries a non-conductive, tubular mesh 122 is configured to be expanded and contracted. A helical conductive wire 124 or other conductor is carried over or woven into the non-conductive mesh. For example, the conductive wire may be a stainless steel braid, but in other instances, the conductive wire can be mono- or multi-filament. Delivery of RF or other electrical energy through the helical conductor 124 will create a helical lesion on the renal pelvis. A helical lesion helps ensure that cross-sectional areas will contain only one unique area of tissue damage around the radius. The diameter of the mesh is 7 Fr-11 Fr in the collapsed state (FIG. 10A) and is 8 mm-20 mm in the expanded state (FIG. 10B). The length of the mesh is 8 mm-20 mm in the expanded state. If the conductive wire is a monofilament, the diameter can be from 0.1 mm to 0.5 mm. If the conductive wire is a braided cable or a braided tube, the diameter can be from 0.1 mm to 0.25 mm. A thermocouple may be secured to the conductive wire or to the non-conductive mesh in proximity to the conductive wire for temperature control. Alternatively, lesions can be created with impedance control only.

In a similar embodiment shown in FIG. 10C, conductive contact pads 126 (e.g. metallic balls) are applied to the conductive wire at specific intervals to enhance tissue contact and create non-continuous lesion patterns. The conductive wire is insulated between the contact pads so that only the contact pads conduct energy to the tissue.

Figure 11A:
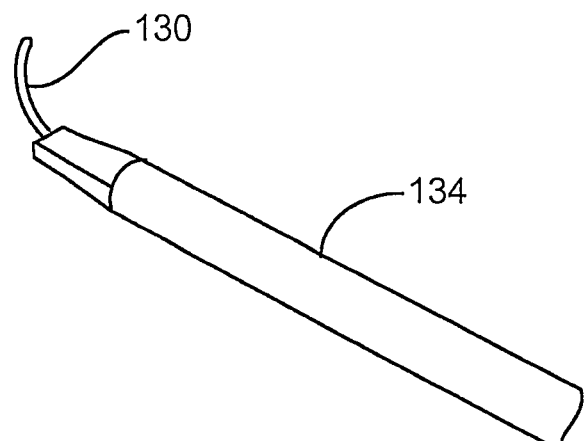
FIGS. 11A-11C illustrate an alternative device configured to create deeper lesions in the renal pelvic wall.
Figure 11B:
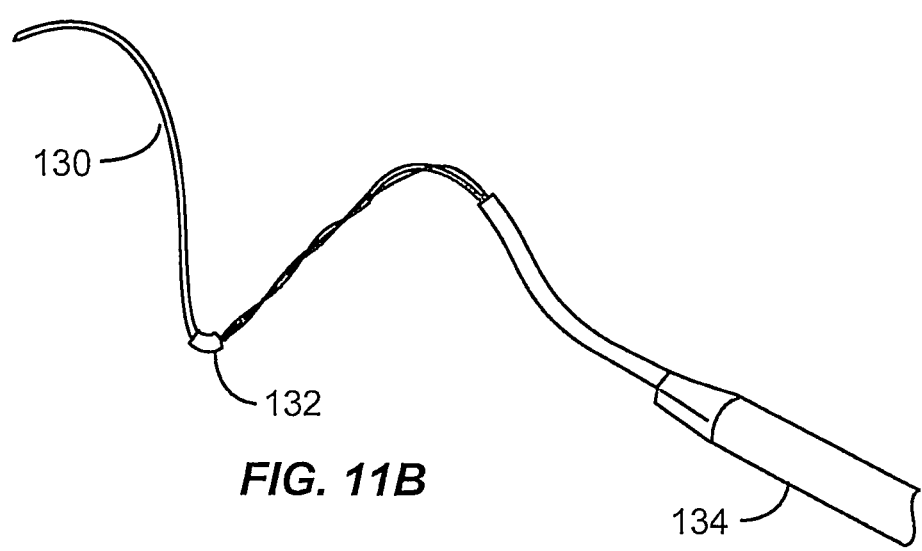
Figure 11C:
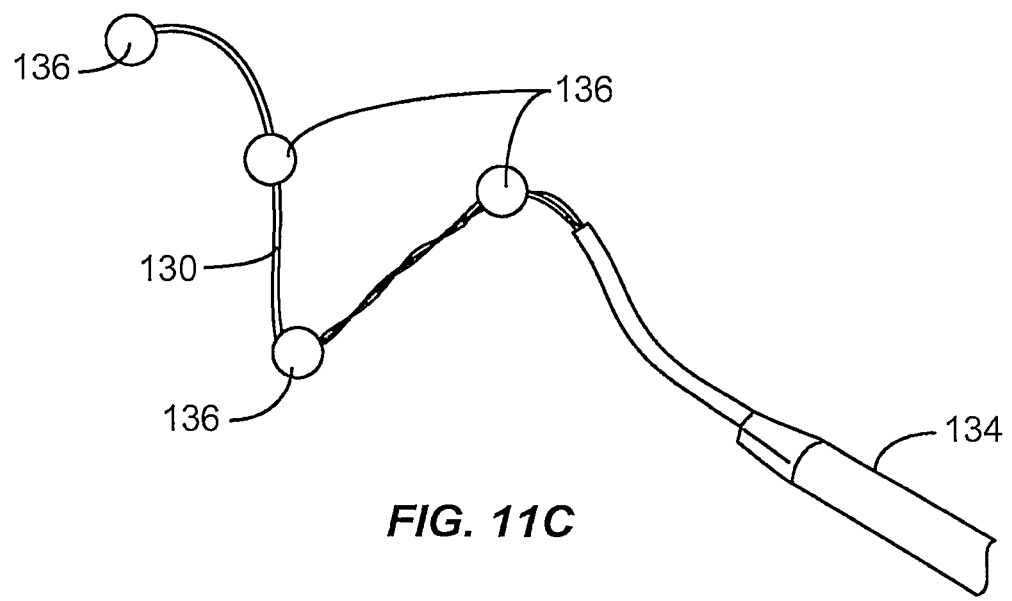

In another embodiment (FIG. 11A-11C), a straight Nitinol® or other superelastic wire 130 or other conductor is heat set into a helical shape at its distal end. An introducer catheter 134 carries the wire and is configured to be advanced to the renal pelvis, typically through the ureter. The wire 130 is then advanced from the lumen of the catheter. As it exits the catheter, the wire 130 assumes a pre-set helical shape. Application of RF through this wire will create a helical lesion in the renal pelvis. A thermocouple 132 may be secured to the wire for temperature measurement. The diameter of the catheter is 7 Fr-11 Fr. The diameter of the helix wire is 8 mm-20 mm in the free-state. The length of the helix is 8 mm-20 mm in the free-state. The diameter of the Nitinol® wire is in the ranges set forth above. In the embodiment of FIG. 11A-B, the helical wire is insulated at certain intervals to create a non-continuous, helical lesion pattern. In the embodiment of FIG. 11C, conductive contact pads 136 (e.g. metallic balls) are attached to the helical wire at specific intervals to enhance tissue contact and create non-continuous lesion patterns. The wire is insulated between the contact pads so that only the contact pads conduct energy to the tissue. Thermocouples are secured inside or proximate to one or more of the contact pads for temperature measurement. The diameter of the contact ball electrodes are in the ranges set forth above.

In another embodiment (FIGS. 12A-12C), a Nitinol® or other superelastic wire 140 or conductor is heat set into a helical shape. The wire is connected to the distal tip of an inner shaft 142 and the distal tip of an outer shaft 146. The inner shaft 142 fits and slides within a lumen of the outer shaft 146. When the inner shaft is extended, the wire is collapsed. When the inner shaft is retracted, the wire opens up into a helical shape. Application of RF through this wire will create a helical lesion in the renal pelvis. A thermocouple (not shown) may be secured to the wire for temperature measurement. The diameter of the outer shaft is 7 Fr-11 Fr. The diameter of the helix wire is 8 mm-20 mm in the expanded state (FIG. 12B). The length of the helix is 8 mm-20 mm in the expanded state. The diameter of the Nitinol® wire is 0.004 in to 0.025 in.

Figure 12A:
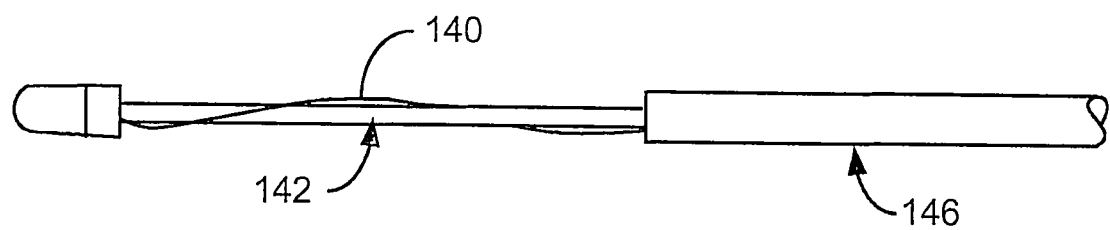
FIGS. 12A-12C illustrate a further alternative device configured to create deeper lesions in the renal pelvic wall.
Figure 12B:
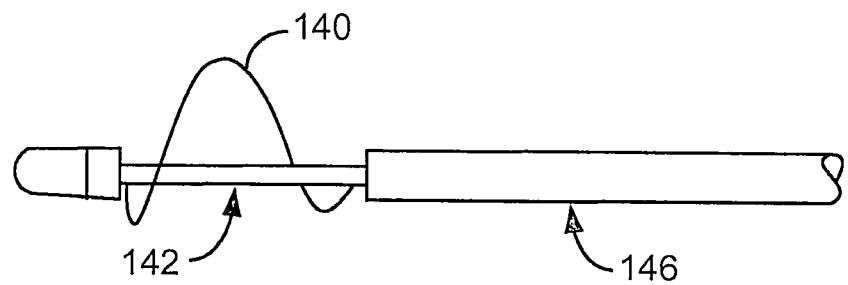
Figure 12C:
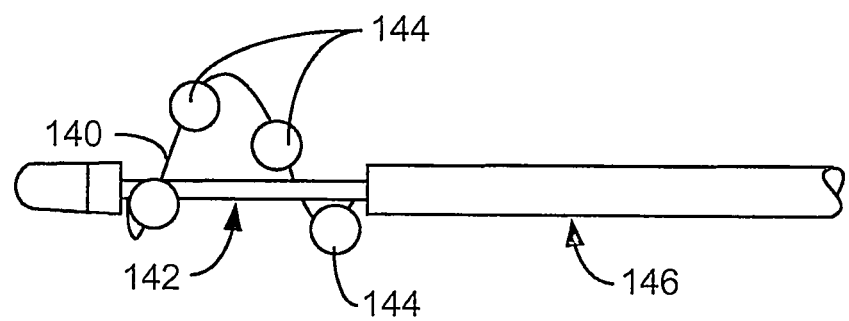

In the embodiment of FIGS. 12A and 12B, the helical wire is typically insulated at certain intervals to create a non-continuous, helical lesion pattern. In the embodiment of FIG. 12C, conductive contact pads 144 (e.g. metallic balls) are applied to the helical wire at specific intervals to enhance tissue contact and create non-continuous lesion patterns. The wire is insulated between the contact pads so that only the contact pads conduct energy to the tissue. Thermocouples are secured inside or proximate to one or more of the contact pads for temperature measurement. The diameter of the contact balls are 0.03 in-0.10 in.

Figure 13:
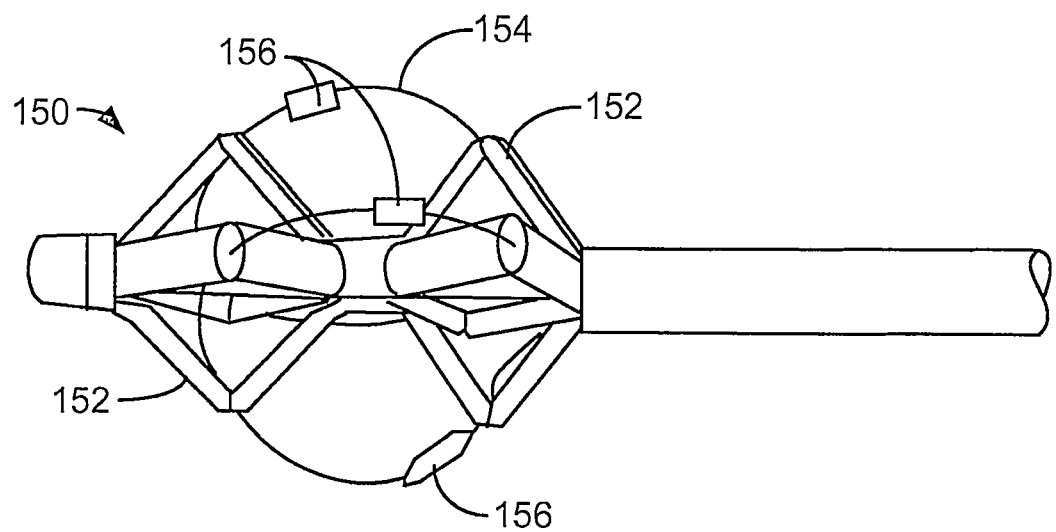
FIG. 13 illustrates a device where the wires carried by malecots have contact pads arranged in a helical pattern.

The device 150 of FIG. 13 includes two malecot supports 152. Wires 154 connect each of the eight ridges or peaks of the malecots, and each of the four wires is insulated except where a larger metallic contact pad 156 is secured. The contact pads are positioned so as to create a helical lesion pattern. Thermocouple(s) (not shown) may be placed on or proximate to one or more of the contact pads for temperature measurement. Wire diameter is 0.004 in to 0.015 in. Length and diameter of the malecots when expanded are typically from 8 mm-15 mm.

Figure 14A:
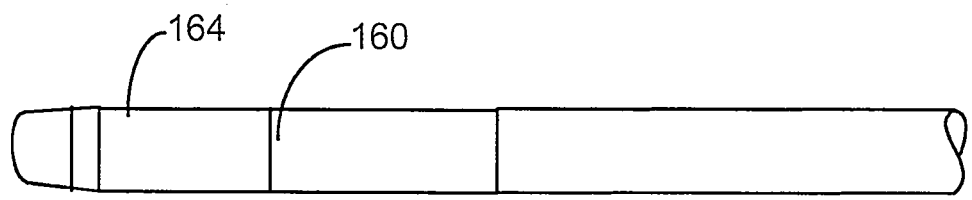
FIGS. 14A and 14B illustrates further alternative devices with deployable tine electrodes arranged in a helical pattern.
Figure 14B:
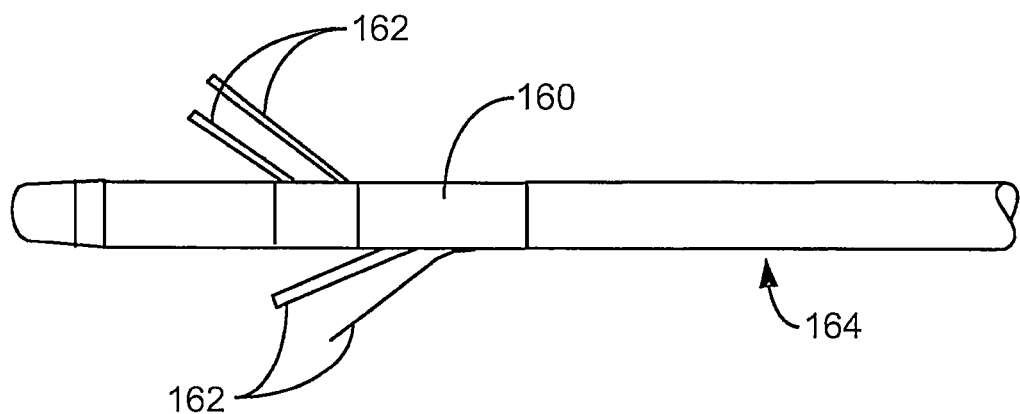

In another embodiment as illustrated in FIGS. 14A and 14B, a Nitinol® or other superelastic tube 160 is laser cut and heat set to form a plurality of outwardly biased tines 162. The tines are axially offset to create a helical pattern, and the tube 160 is electrically insulated except for the distal ends of the tines. The tube is secured to a catheter shaft (not shown), and a sheath 164 slides over the tube and catheter. As the sheath is slid distally, the tines are exposed and allowed to expand outward to contact the tissue. Application of RF energy will create discreet lesions in a helical pattern. Thermocouples (not shown) may be secured to the inside of one or more of the tines for temperature measurement. The sheath diameter is 7 Fr to 11 Fr. The tips of the tines expand to create a helix with a diameter of 8 mm-20 mm.

Figure 15:
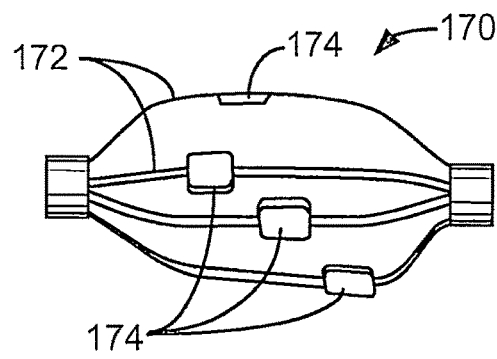
FIG. 15 illustrates another self-expanding support structure carrying a helical arrangement of electrode contact pads.
Figure 20:
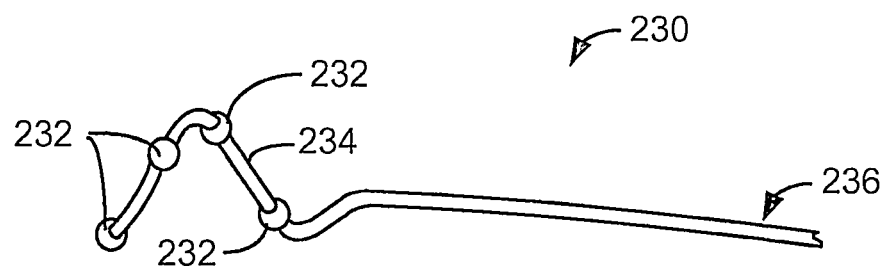
FIGS. 20-23 illustrate a renal wall ablation device similar to that of FIGS. 11A-11C.
Figure 21:

In yet another embodiment (FIG. 15), a Nitinol® or other superelastic tube is laser cut and heat set so as to create a self-expanding bulb 170 with a plurality of struts 172 which carry contact pads 174. The tube is electrically insulated, except for the contact pads. FIG. 20 shows the laser cut tube only, but the tube would be secured to a catheter shaft (similar to any of the catheter shafts shown previously) at proximal end of the tube. A sheath is slid over the tube to contract the bulb. As the sheath is slid proximally, the bulb opens and the contact pads expand to contact the tissue. Thermocouples may be secured to the inside of one or more of the tines for temperature measurement. Application of RF energy will create discreet lesions in a helical pattern. The sheath diameter is 7 Fr to 11 Fr, and the bulb expands to a diameter of 8 mm to 20 mm.

In still other embodiments, a single ball-electrode may be disposed at the distal end of a steerable catheter and may be used to create discreet lesions one-at-a-time. The user positions the ball to contact the tissue at the appropriate spots. The electrode can be monopolar or bipolar. A thermocouple may be secured inside or proximate to the ball for temperature measurement. The ball diameter is typically 0.02 in-0.10 in.

As an alternative to targeting the nerves embedded close to the surface the wall of the renal pelvis, it may be advantageous to target the nerves further away from the renal pelvic wall (e.g. nerves surrounding the renal arteries). The inventors herein have found that damaging the wall of the renal pelvis may be detrimental to proper function. Therefore, in these other embodiments, it would be advantageous to target nerves farther away from the renal pelvic wall, while leaving the renal pelvic wall intact. In addition, it would be advantageous to do this by accessing the renal pelvis, or anywhere along the ureter or kidney. Previously described ultrasound catheters deliver acoustic energy "to heat the wall of the renal pelvis and renal nerves embedded in the tissue bed surrounding the renal blood vessels". This achieves reaching the farther nerves. In order to lessen risk of damaging the renal pelvic wall, the present invention can employ "focused" ultrasound transducers (high intensity focused ultrasound or HIFU) which can directly heat tissue surrounding the target nerves with minimal heating of the pelvic wall and the tissues immediately adjacent to the pelvic wall. Thus, an ultrasonic transducer catheter can access the renal pelvis through the ureter and deliver energy to tissue beyond the renal pelvic wall while keeping the renal pelvic wall intact with minimal heating.

Catheters according to the present invention may comprise tissue-penetrating elements in addition to the radiation-emitting elements which have been previously described. For example, the tissue-penetrating elements may comprise radio frequency electrodes, chemical delivery structures, heat delivery structures, cryogenic delivery structured, and the like.

The devices described above are mainly intended for transuretheral approaches. Most of these designs, however, are also suitable for a vascular approach where the renal nerves are targeted by passing a catheter through the renal artery and creating lesions through the artery. Current vascular approach renal denervation devices typically create helical lesions. Thus, all of the above designs that create helical lesions can be adapted for the vascular approach. Catheter sizes for such a vascular approach are in the range from 4 Fr to 8 Fr.

Figure 16:
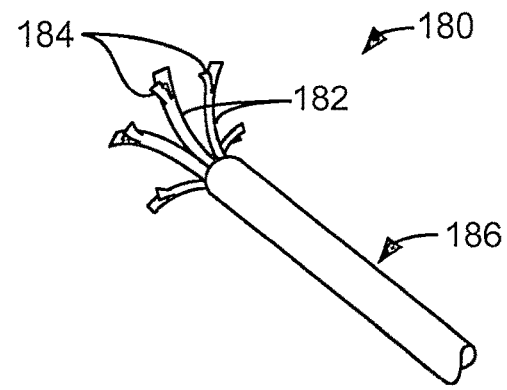
FIGS. 16-19 illustrate tools configure to mechanically disrupt nerves in the renal pelvis wall.

The renal nerve pathways may also be disrupted by mechanical means. In one embodiment, as illustrated in FIG. 16, an expandable member 180 is formed from a laser cut Nitinol® or other superelastic tube that is heat set with expandable tines 182 and bent up tabs 184 that act as cutters. A sheath 186 may be advanced to collapse the tines inside the sheath. When the sheath is retracted, the tines self-expand outwardly so that the cutters can contact with the wall of the renal pelvis. The device is then rotated and/or translated axially so as to scrape the inner wall of the renal pelvis. This scraping will disrupt the nerves at the surface of the renal pelvis wall. In order to control bleeding, a balloon can be inserted into the renal pelvis after the scraping to apply pressure to the walls. The sheath size for this device is 7 Fr to 11 Fr. Various other embodiments for mechanical renal denervation can also be used including a single scraper consisting of a curved member with a sharp distal area and an expandable stent-like device with various sharp areas.

Figure 17:
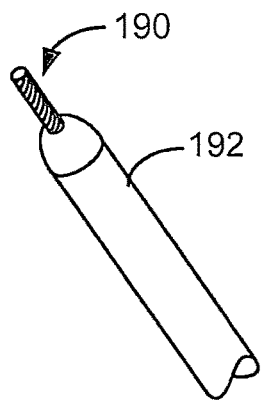

In another embodiment, as shown in FIG. 17, mechanical denervation may be done using high frequency vibration. High frequency vibration has been used in other medical devices for such purposes as tunneling and boring. In this embodiment, a tip or "effector" 190 may have various geometries, may be delivered via a catheter 192, and may be placed on the urothelium of the renal pelvis where it is driven by a generator such as a piezoelectric or other transducer to provide high (>1000 Hz) or low (<1000 Hz) frequency energy where the resulting vibration for causes scraping and/or abrading of the surface of the urothelium to disrupt nerves. The tip 190 may be retractable in the catheter 192. Such vibratory catheters will typically be sized from 7 Fr to 11 Fr. Other suitable effector geometries may include but are not limited to (1) rectangular, flat surface area, (2) helical surface area, (3) effector of curved geometry for enhanced contact with the renal pelvis, and (4) steerable effector for targeted contact with the renal pelvis.

Figure 18:
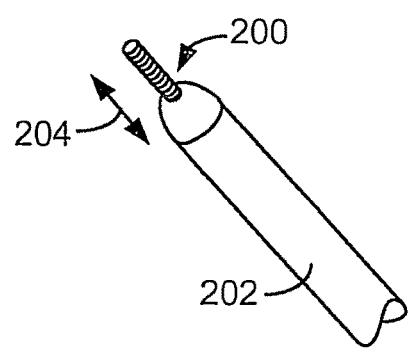

In still another embodiment as illustrated in FIG. 18, mechanical denervation may be accomplished via a reciprocating motion. A shaft 200 is reciprocated axially (the direction of arrow 204) within a larger catheter shaft 202 and can abrade the surface of the renal pelvis. An inner telescopic shaft may be knurled or of similar geometry to cause abrasion for the purpose of denervation. Such reciprocating-element catheters will typically be sized from 7 Fr to 11 Fr. Other suitable shaft geometries include but are not limited to (1) a shaft tip with curved geometry for enhanced contact with the renal pelvis, and (2) a steerable tip for targeted contact with the urothelium of the renal pelvis.

Figure 19:
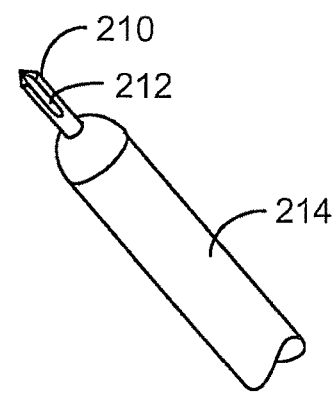

Mechanical denervation may also be accomplished using tools similar to those used for tissue biopsy, as shown in FIG. 19. Such tool would include a needle element 210 having a groove 212. The needle would reciprocate from a catheter 214 and be used to remove small amounts of the renal pelvis in strategic locations. Many biopsy devices exist for various parts of the body. This embodiment, however, would be specific to the renal pelvis and for the purposes of excising small portions of the pelvis layers in an effort to capture and disrupt renal nerves. The catheter size for this device is 7 to 11 Fr. Various other biopsy geometries and elements may include but are not limited to (1) a cannulated sheath to cover the needle tip with our without circumferential rotation for the purposes of aiding tissue excising, (2) a curved geometry for enhanced contact with the renal pelvis, and (3) a steerable device for targeted contact with the renal pelvis.

Referring now to FIGS. 20-23, a device 230 for deploying helically disposed ball electrodes 232 on a pre-shaped wire 234 will be described. The wire 234 may be a superelastic Nitinol® wire having a distal end that is set into a helical or spiral shape. The plurality of metal balls 232 (four being illustrated in the drawings but anywhere from two to ten typically being useful) are attached to the wire 234 and heat shrink tubing 236 is placed over a proximal length of the wire and between the balls for insulation. A thermocouple may be attached to the most proximal ball. The Nitinol® wire diameter is typically 0.4 mm. The ball diameter is typically 12 mm. When the insulation is applied over the wire, it typically has a wall thickness of 0.1 mm and an outer diameter of typically 0.6 mm. A smaller wall thickness can be obtained by replacing the heat shrink tubing with a dielectric coating. The helical pitch is typically 12 mm. The pitch diameter (through the center of the wire) is typically 0.8 mm. The wire will be delivered through a sheath 238 which is steerable at the distal end, either being shapeable or pre-shaped. The sheath typically has an inner diameter of 2.1 mm and an outer diameter of 2.6 mm.

Figure 24:
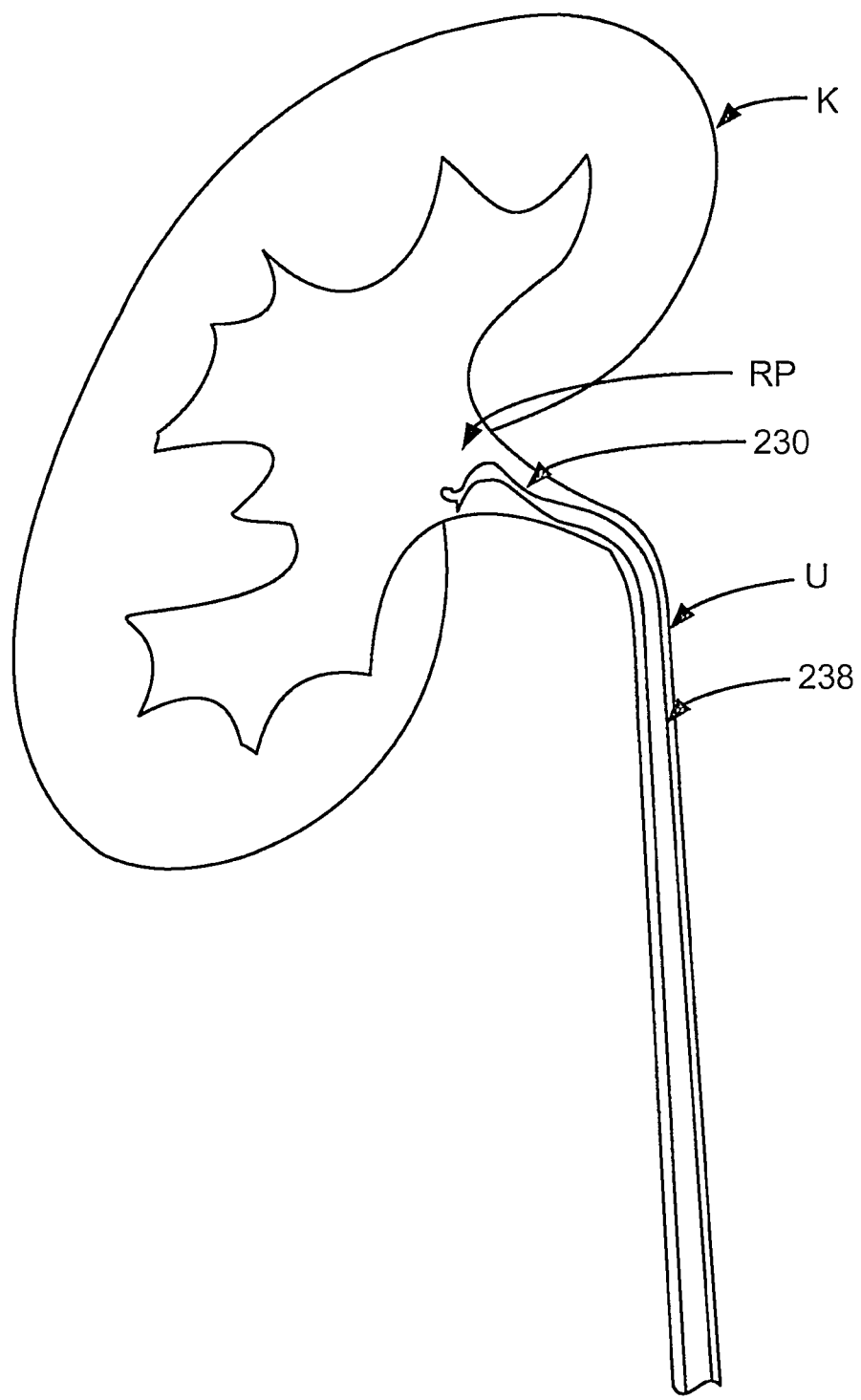
FIG. 24 illustrates use of the device of FIGS. 20-23 in ablating a renal pelvis wall.

The device 230 may be delivered to the renal pelvis RP as shown in FIG. 24. A guidewire (not shown) is first passed through the urethra, into the bladder, into the ureter U, and up to the kidney K. A dilator (not shown) is placed into the center lumen of the sheath 238. The dilator and sheath are then threaded up the guidewire into ureter and positioned so that the distal end of the sheath is just proximal of the renal pelvis. The guidewire and dilator are then removed, leaving just the sheath in place. The device 230 is then inserted through the sheath until the helical portion exits the distal end. The sheath can then be steered to position the device in the center of the renal pelvis. RF energy is then applied to the device and lesions are created at the ball/tissue interface.

In alternative configurations, each ball electrode can be independently turned on/off. A separate thermocouple can be fixed to each ball to monitor independent ball temperatures. The electrodes/wire can be stamped as shown in the Figure. These designs can be scaled down for renal denervation through the renal artery instead of through the renal pelvis.

Figure 25:
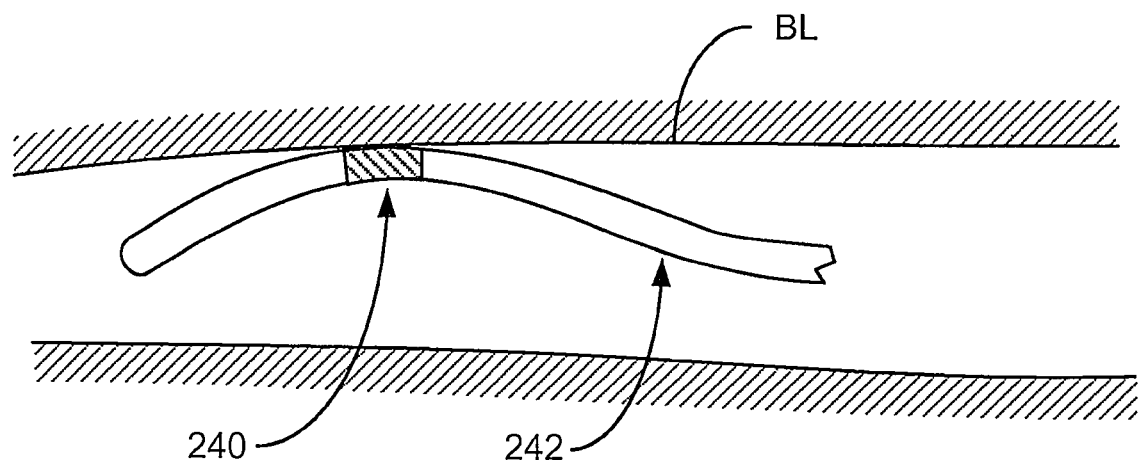
FIGS. 25 and 26 illustrate the use of device with cylindrical electrodes and spherical electrodes for ablating a luminal wall.
Figure 26:
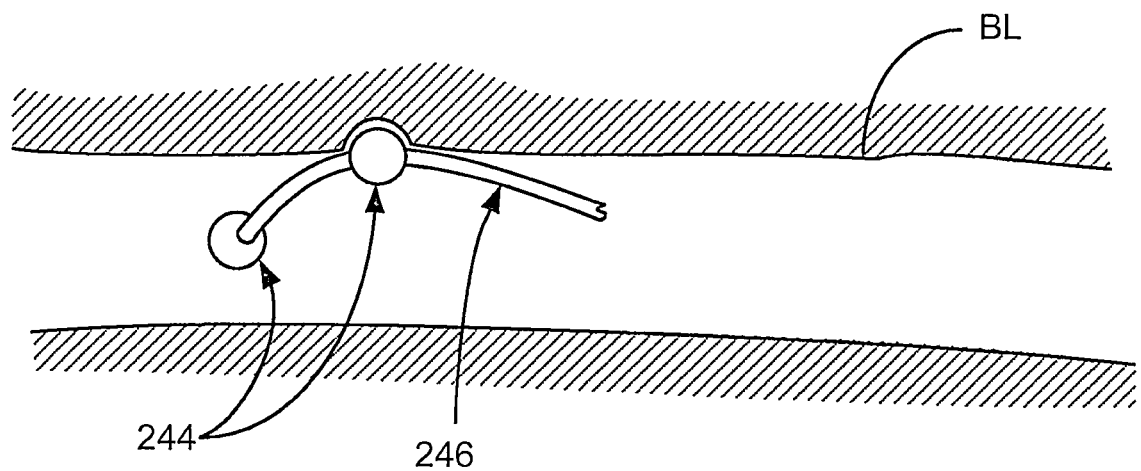

As shown in FIGS. 25 and 26, a cylindrical or "band" electrode 240 carried on a catheter or wire 252 will have only moderate contact with the wall of a body lumen BL. A relatively large ball electrode 244, however, carried on a smaller wire 246, will embed into the wall and provide a much greater surface contact area with the wall of the body lumen BL than a conventional band electrode.

As shown in FIGS. 27A-27C, a vacuum can be applied inside the ureter and/or renal pelvis to collapse the walls of the kidney. This technique can be very useful to help bring the tissue throughout the renal pelvis into intimate and conforming contact with electrodes and other mechanical effectors, as shown for example in FIG. 27C. All devices described in herein can benefit from such vacuum application and kidney wall collapse, but most if not all of the devices can function with no or only a partial collapse. This vacuum-assisted approach is not intended to be applied to vascular renal denervation approaches.

As shown in FIG. 27A, an ablation device 300 comprises a Nitinol® or other superelastic nickel-titanium alloy wire 302 with ball electrodes 304 attached. When deployed through a catheter 306 into the renal pelvis RP, the wire takes on a shape similar to pelvis. The assumed shape typically occupies a three-dimensional within the renal pelvis to help engage or approximate balls against the tissue surface of the inner renal pelvic wall. Vacuum is applied, typically through a lumen of the catheter 306 to help embed the balls into tissue surface. RF energy is applied through the wire to the balls to create discreet lesions, damaging the renal nerves. The wire can optionally be pre-shaped in order to approximate the shape of the pyramids surrounding the renal pelvis.

Figure 28A:
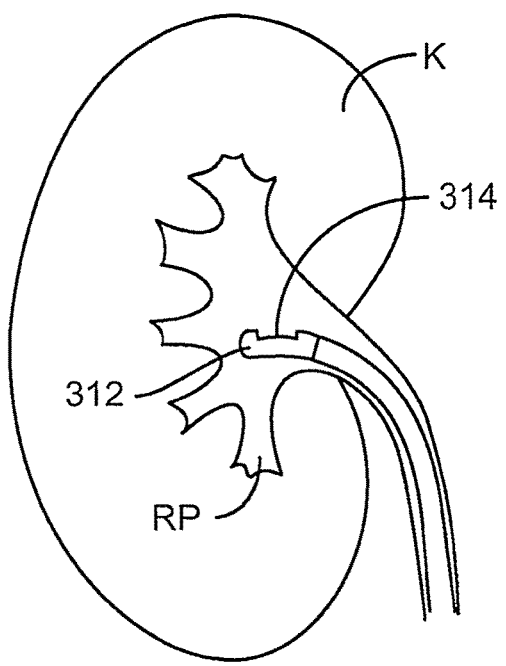
FIGS. 28A-28C show a catheter with a cutting blade inside the renal pelvis.
Figure 28B:
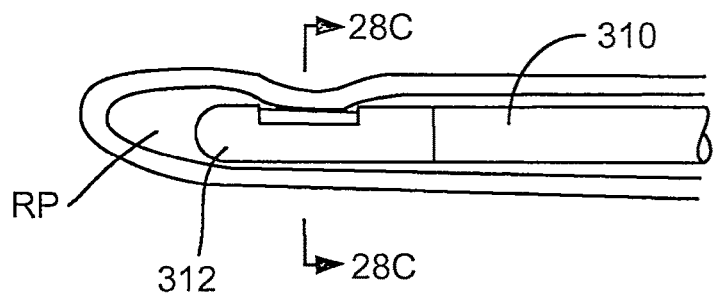
Figure 28C:
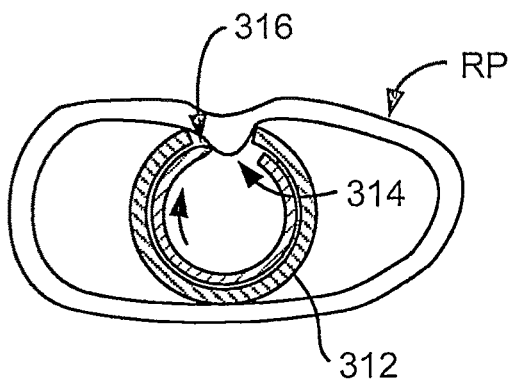

As shown in FIGS. 28A-28C, a mechanical cutter 312 is attached to a distal end of a catheter 310 having a cutting slot 314. A vacuum may be applied to draw tissue into the cutter slot 314 and a cylindrical blade 316 may be rotated to excise a small piece of tissue. Removal of renal pelvic tissue in this manner will sever renal nerves.

Figure 29A:
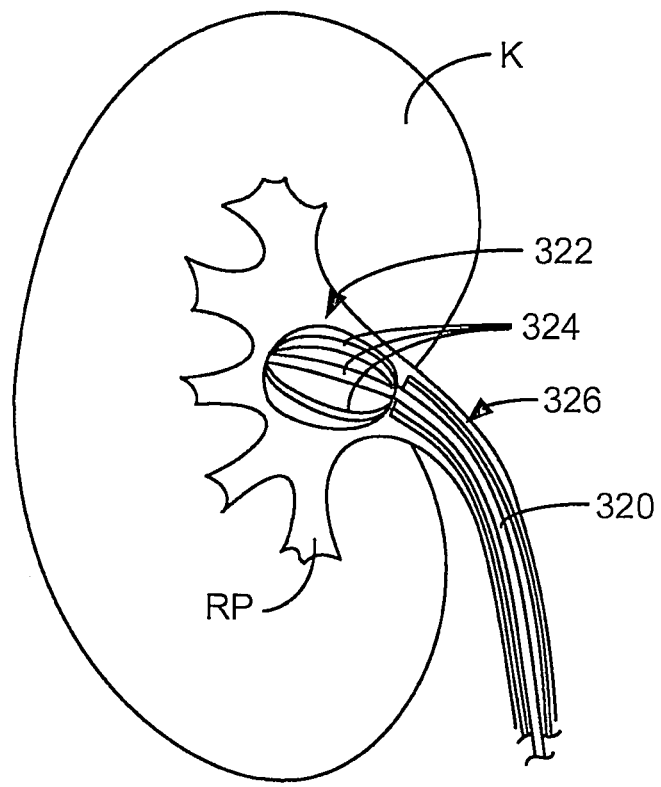
FIGS. 29A and 29B show a balloon with abrasive strips attached to the outsides deployed inside the renal pelvis.
Figure 29B:
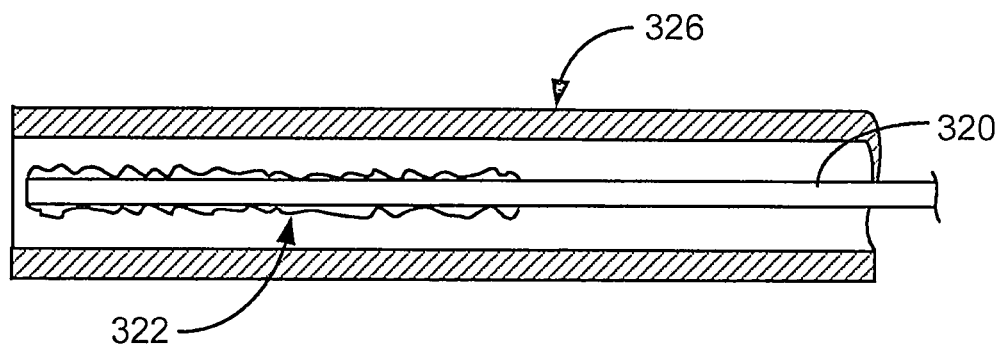

As shown in FIGS. 29A and 29B, a catheter 320 carries a distal balloon 322 having a plurality of abrasive strip 324 thereon. The balloon on the catheter may be deployed into the renal pelvis RP and, once inside the renal pelvis, a vacuum is optionally drawn and the balloon is rotated and/or translated to abrade the tissue surface. Such abrasion damages the renal nerves.

Figure 30A:
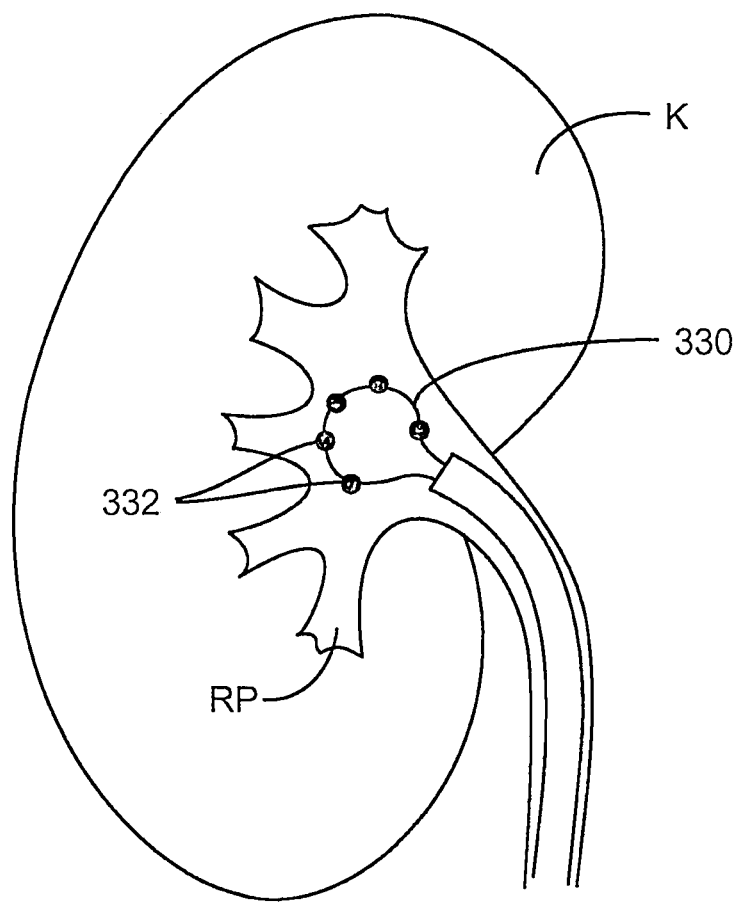
FIGS. 30A and 30B show a superelastic alloy loop wire with abrasive balls attached to the distal end.
Figure 30B:
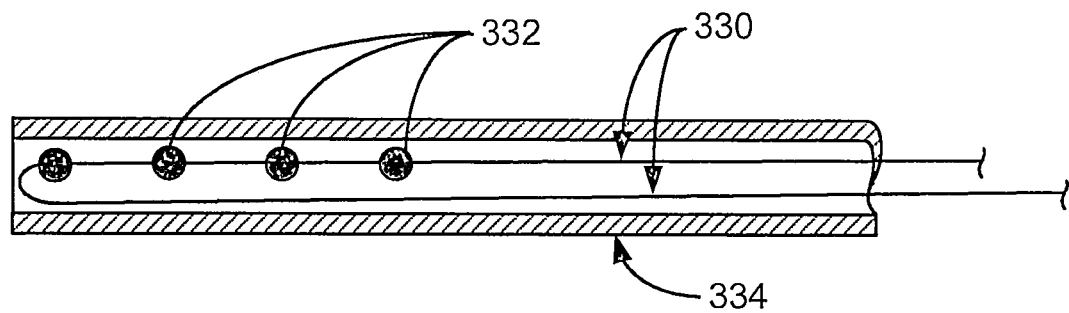

As shown in FIGS. 30A and 30B, a Nitinol® or other elastic wire 330 carries a plurality of abrasive balls 332. The wire 330 is preferably formed into a loop structure so that it expands across the renal pelvis when it is advanced from a delivery sheath or catheter 334. Once deployed, a vacuum is optionally applied, and the wire loop and balls are rotated and/or translated to abrade the tissue surface. This abrading damages the renal nerves.

Figure 31A:
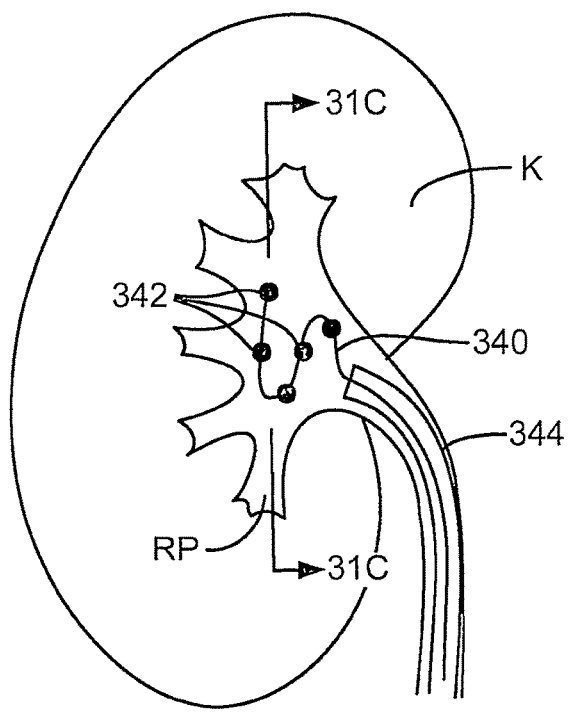
FIGS. 31A-31C show ball electrodes on a superelastic alloy wire deployed out of a sheath and into the renal pelvis where the wire takes on a serpentine shape.
Figure 31B:
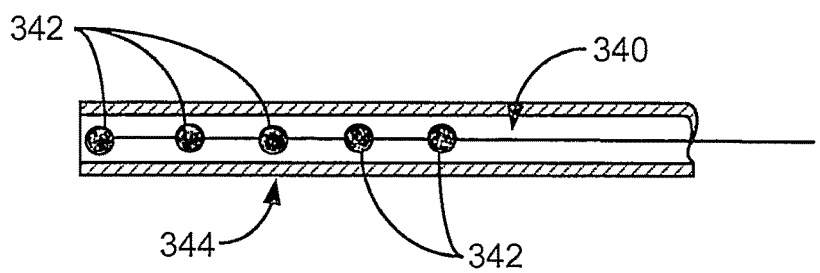
Figure 31C:
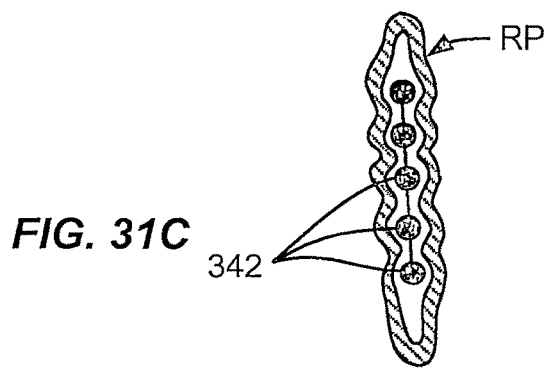

As shown in FIGS. 31A-31C, a Nitinol® or other elastic wire 340 carries a plurality of ball electrode 342. When deployed into the renal pelvis RP, the wire 340 is pre-shaped to assume a two-dimensional serpentine shape. Vacuum is optionally applied to help embed the electrode balls into tissue surface. RF energy is applied through the wire to the balls to create discreet lesions, thus damaging the renal nerves. Alternatively, the wire shape can be pre-shaped in a circular, semi-circular, linear, spiral, or any other geometry with proximal and distal ends.

Figure 32A:
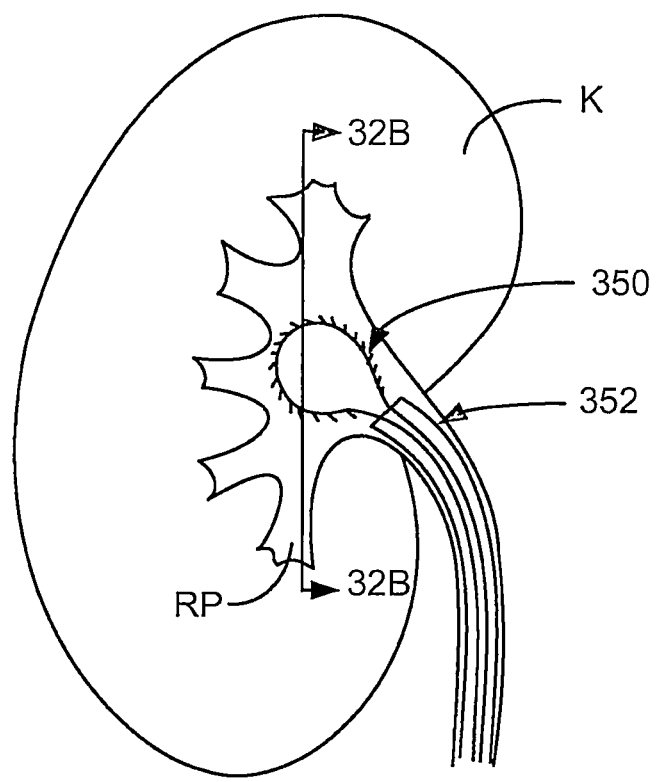
FIGS. 32A and 32B show a saw-tooth wire loop both inside a sheath and deployed in the renal pelvis.
Figure 32B:
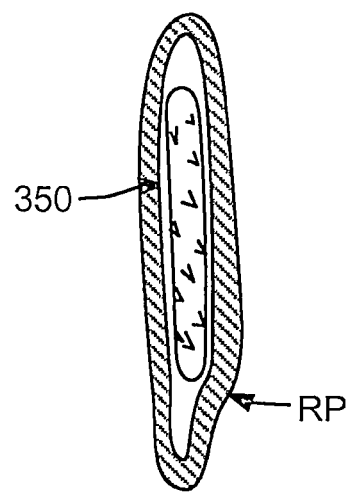

As shown in FIGS. 32A and 32B, a Nitinol® or other elastic wire 350 is formed with saw-teeth and deployed from a catheter or sheath 352 into the renal pelvis RPs. Once deployed, the saw-tooth wire can be translated and/or rotated to cut and/or abrade the tissue lining the inner wall of the renal pelvis. Applying a vacuum to the renal pelvis will help to keep the tissue in contact with the wire. This cutting/abrading damages the renal nerves.

Figure 33C:
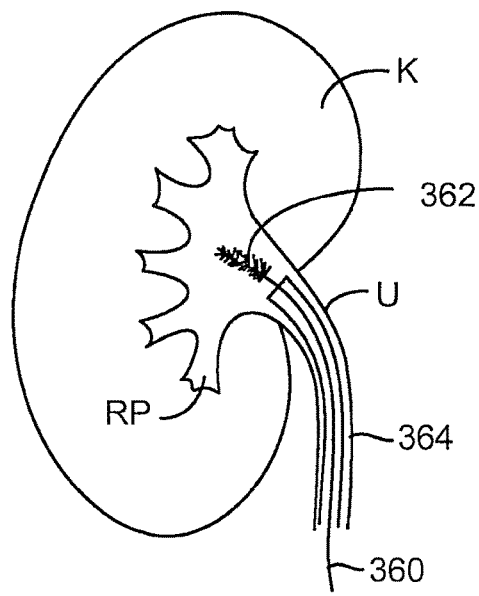
FIGS. 33A-33D show a wire brush and balloon tamponade both inside a sheath and deployed in the renal pelvis.
Figure 33A:
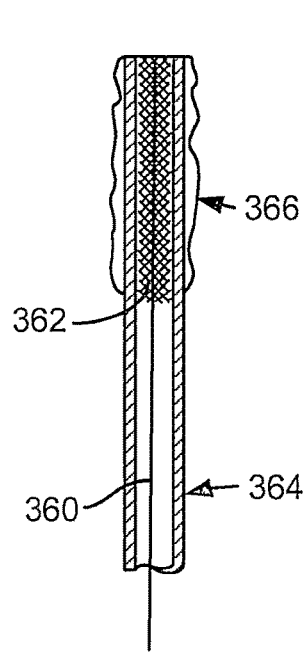
Figure 33B:
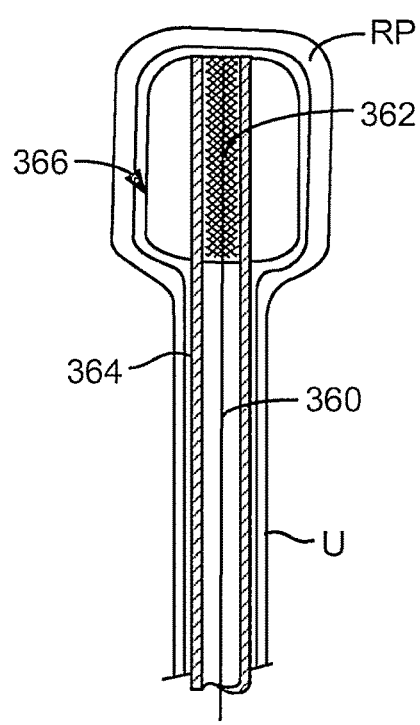
Figure 33D:
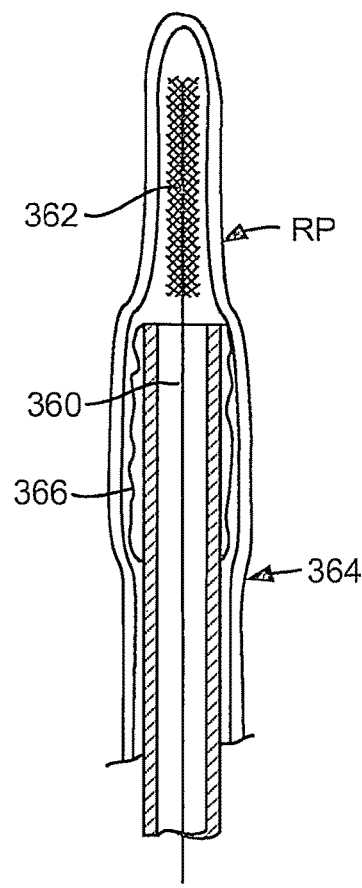

As shown in FIGS. 33A-33D, a Nitinol® or other elastic wire 360 carries a wire brush 362 which in turn is carried within a lumen of a catheter 364 having a distal balloon 366. The brush 362 is deployed from the ureter U into the renal pelvis RP, as shown in FIGS. 33B and 33C. The brush is then rotated and/or translated to abrade the tissue surface. A vacuum can be applied to help keep the tissue in contact with the brush. This abrading damages the renal nerves. After abrading, the brush is returned to the inside of the catheter. The balloon is then deployed inside the renal pelvis (FIG. 33D) to act as a tamponade and stop bleeding from the abraded tissue. The balloon may optionally have electrodes or other current delivery elements to apply electrocautery.

Figure 34C:
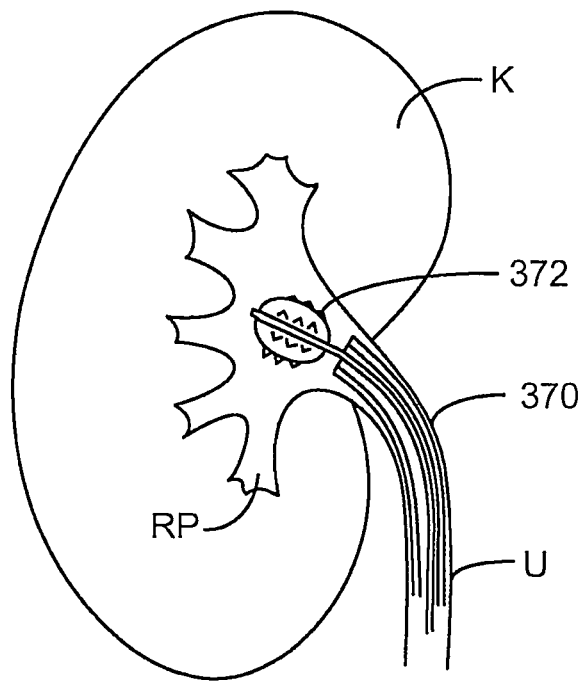
FIGS. 34A-34C show a drug delivery balloon with microspikes both inside a sheath and deployed in the renal pelvis.
Figure 34A:
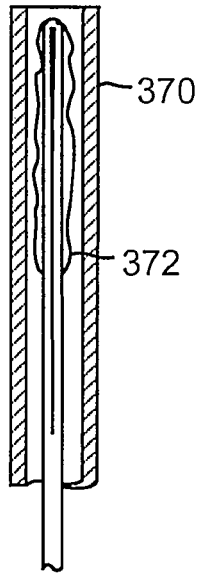
Figure 34B:
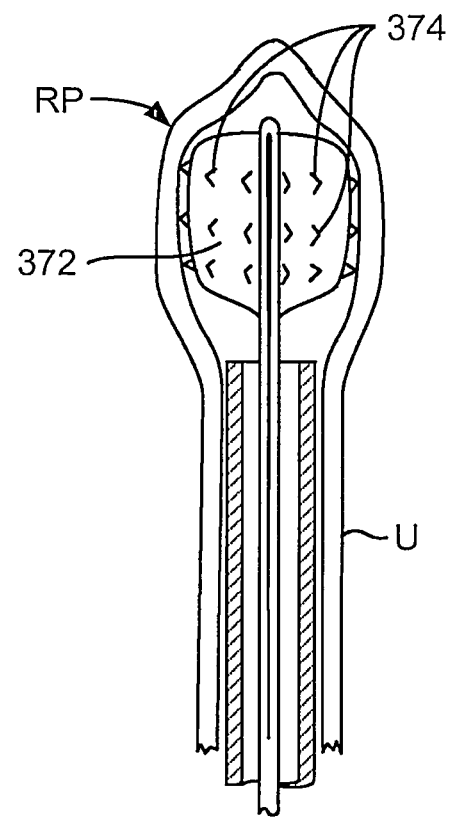

As shown in FIGS. 34A-34C, a catheter 370 carries a distal balloon 372 having a plurality of micro-spikes 374 thereon. The balloon on the catheter may be deployed into the renal pelvis RP and, once inside the renal pelvis, a vacuum may be drawn and the balloon will be inflated and rotated and/or translated to abrade the tissue surface. Such abrasion damages the renal nerves. The micro-spikes may optionally be hollow to deliver therapeutic or other agents to the wall of the renal pelvis either before, during, or after the abrasion. An exemplary agent is ethanol which will deactivate the nerves.

Figure 35A:
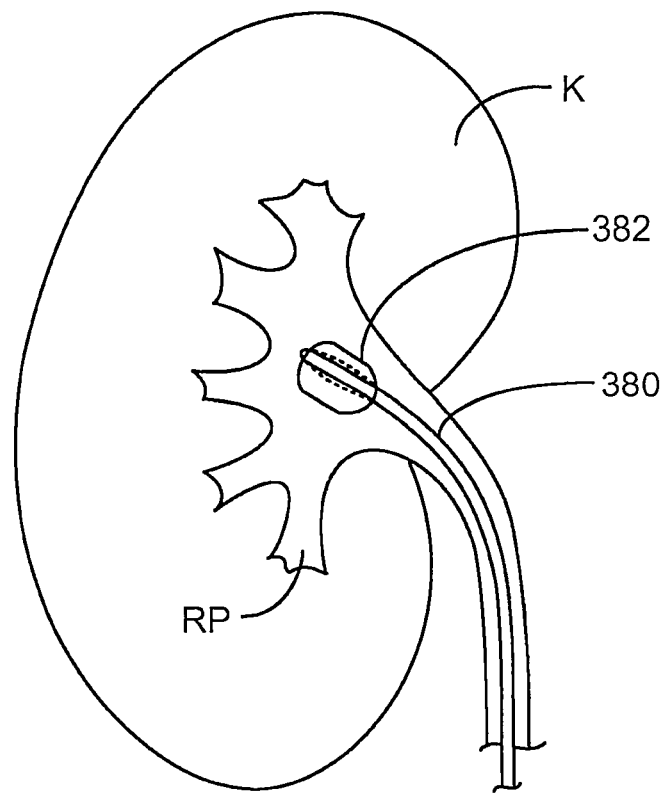
FIGS. 35A and 35B show a drug delivery balloon with openings on top and bottom sides to direct drug delivery to specific tissue areas.
Figure 35B:
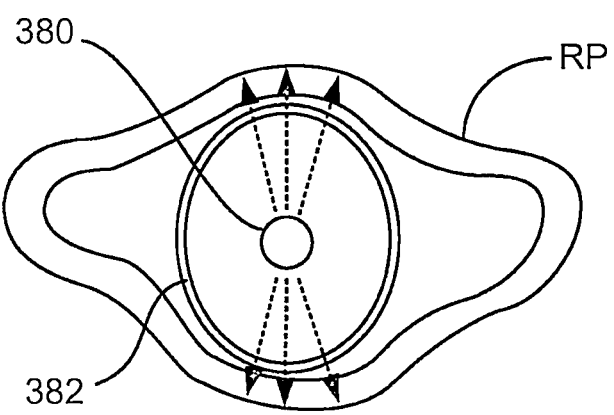

As shown in FIGS. 35A and 35B, a catheter 380 carries a distal balloon 382 having a plurality of infusion holes or ports thereon. The holes are typically deposed on the top and bottom of the balloon so that they will deliver substances directly into the wall of the renal pelvis RP, as shown in FIG. 35B. Preferably, a vacuum is applied to the renal pelvis to engage the holes against the tissue for targeted placement.

Figure 36A:
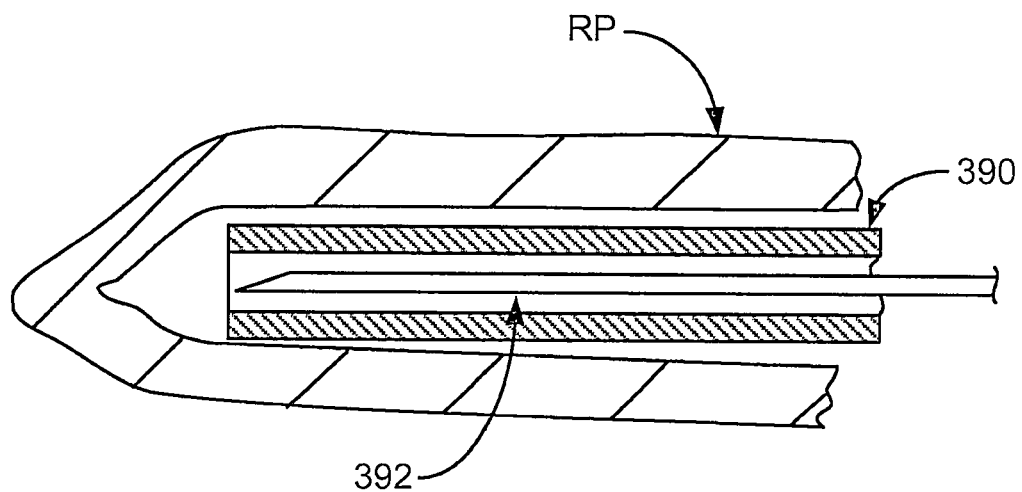
FIGS. 36A and 36B show a catheter with drug delivery needle both inside a sheath and deployed into the renal pelvic tissue.
Figure 36B:
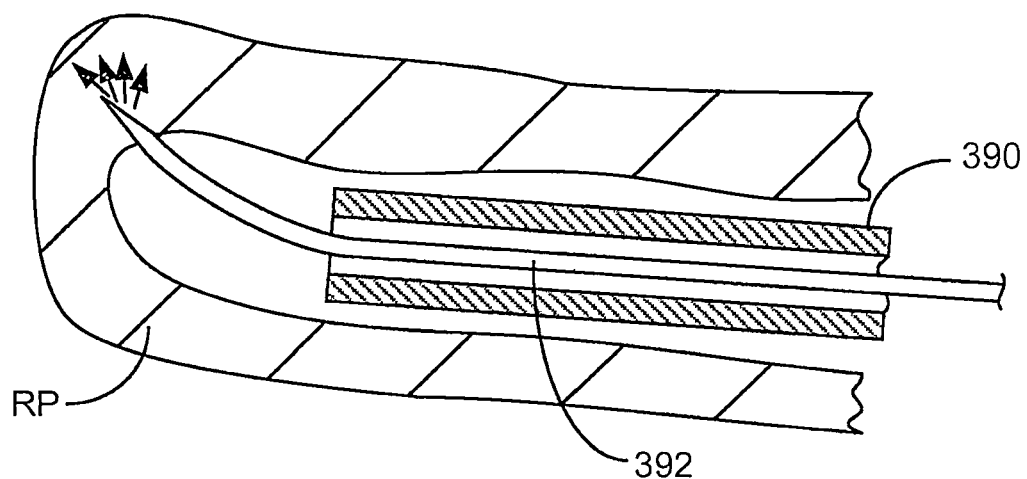

As shown in FIGS. 36A and 36B, a catheter 390 carries a deployable needle 392. The catheter is positioned inside the renal pelvis RP, and the needle is deployed, to pierce through the wall of the renal pelvis. Agents such as ethanol can then be delivered through the needle into the tissue to deactivate the renal nerves. Note that while the figures show the needle deploying from the distal tip of the catheter, the needle or a plurality of needles can alternatively exit through side holes in the catheter. A vacuum will preferably be used to approximate the tissue to the catheter and facilitate needle penetration.

Figure 37:
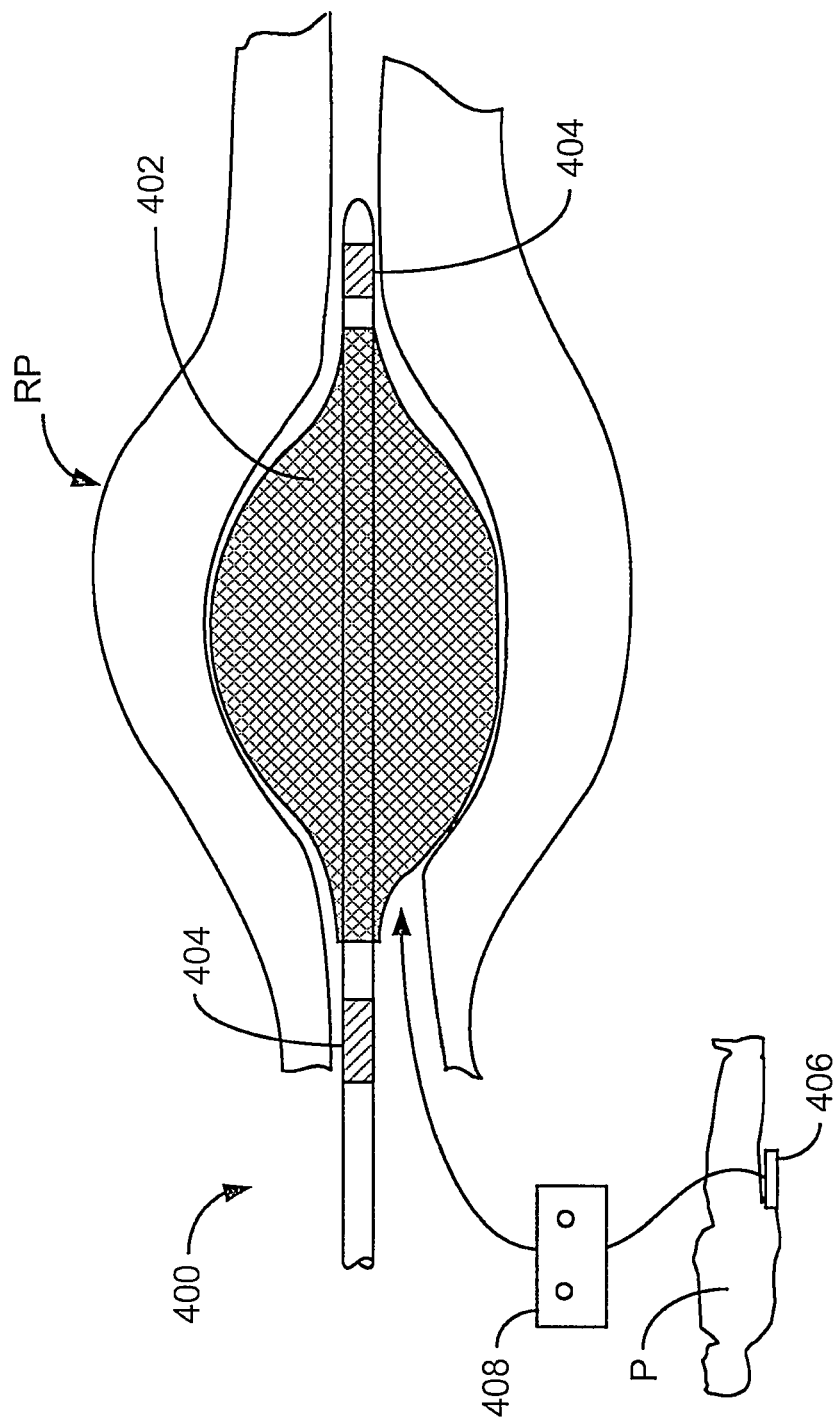
FIG. 37 shows a catheter system with expandable mesh for iontophoretic drug delivery.
Figure 38A:
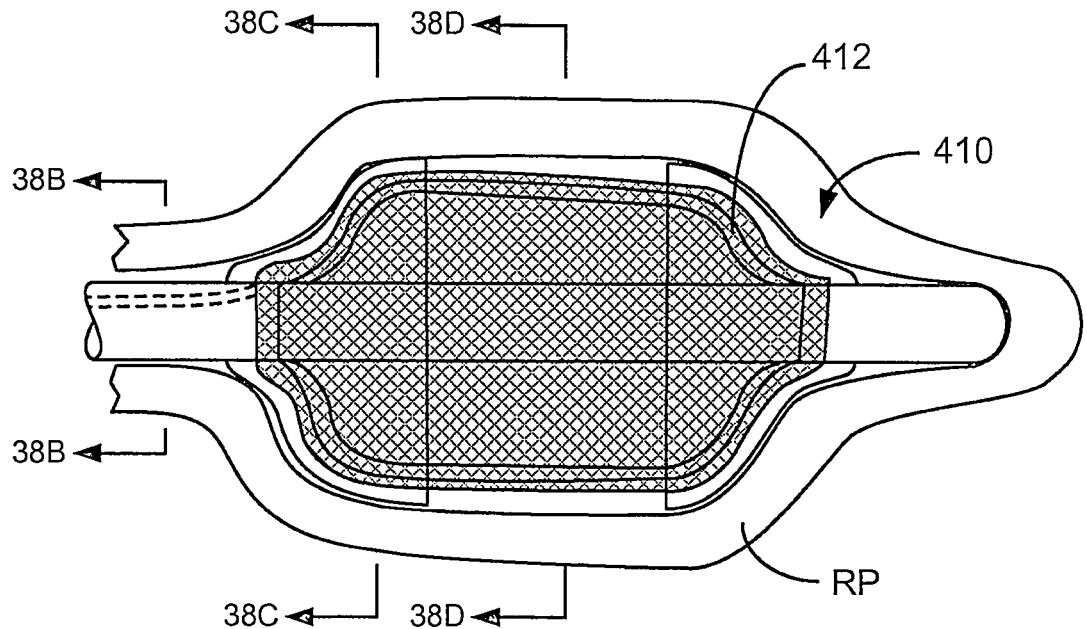
FIGS. 38A-38D show a drug delivery catheter with mesh, silicone, and balloon components.
Figure 38B:
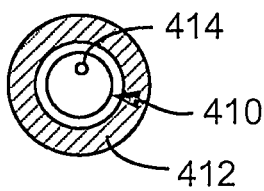
Figure 38C:
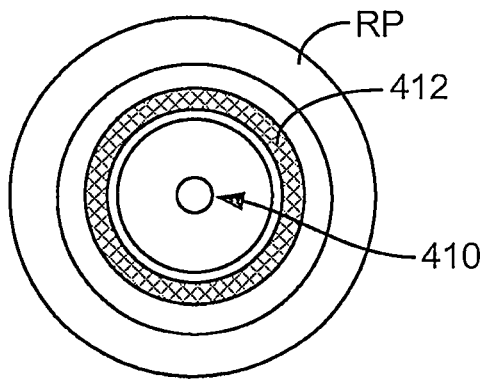
Figure 38D:
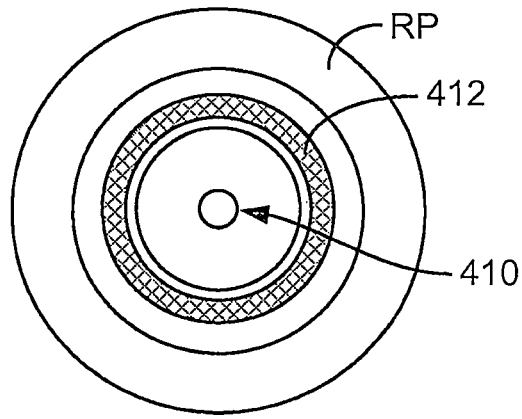
Figure 39:
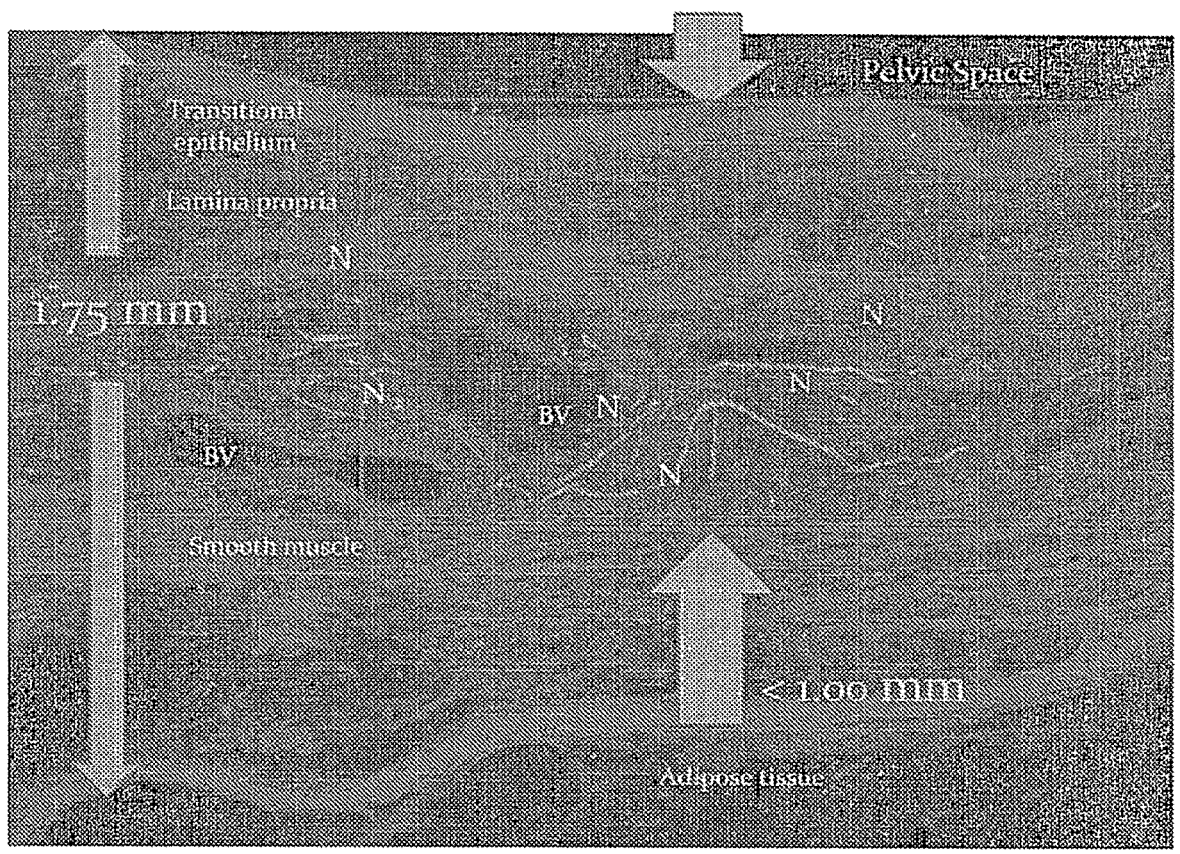
FIG. 39 shows a magnified cross section of renal pelvic tissue with the letter "N" illustrating nerves.
Figure 40:
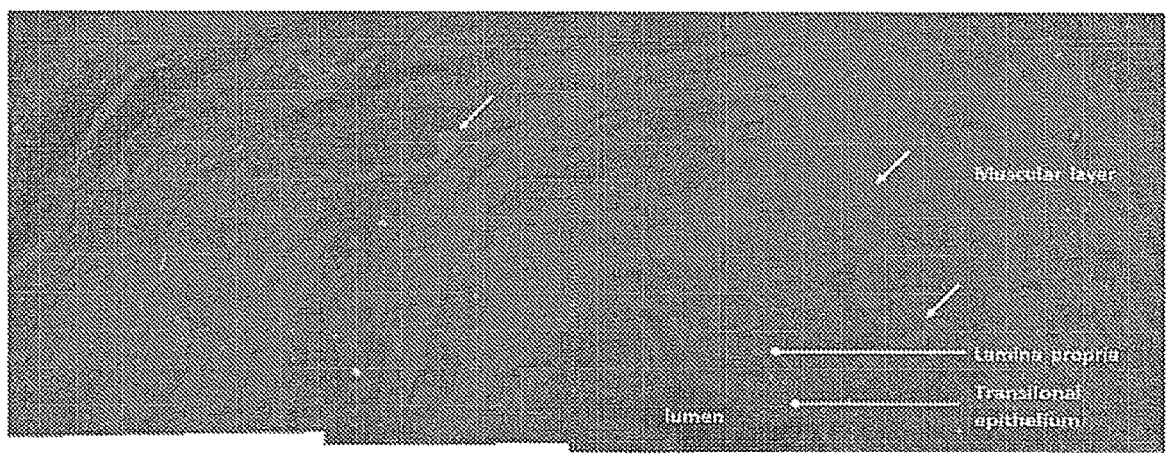
FIGS. 40-42 show magnified cross sections of ureteral tissue with arrows pointing to nerves.
Figure 41:
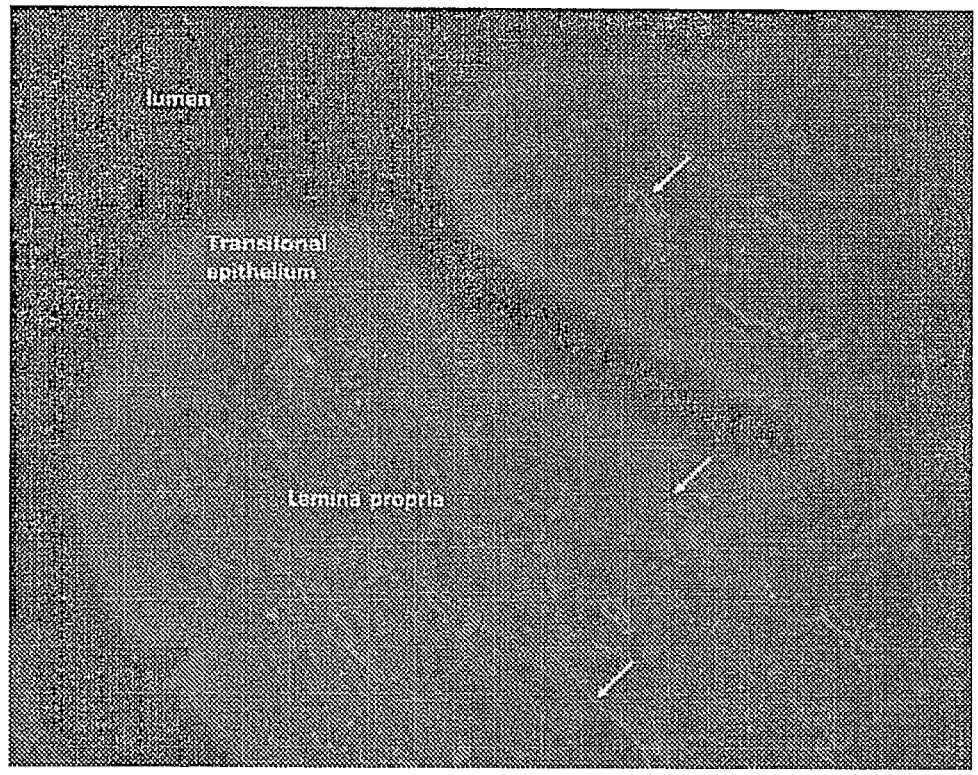
Figure 42:
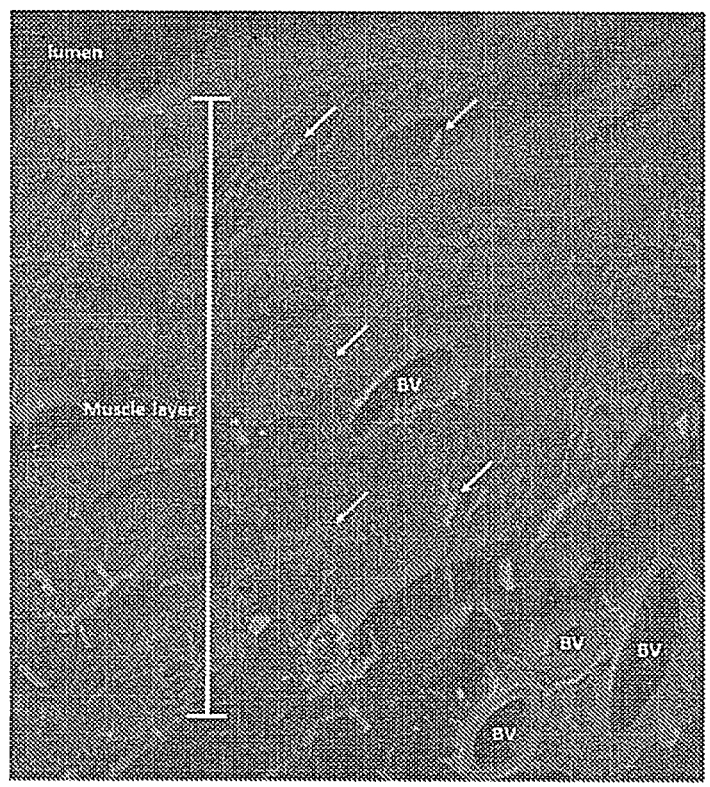

As shown in FIG. 37, an iontophoresis catheter 400 carries an electrically conductive, radially expansible cage 402 at its distal end. Iontophoresis is a physical process in which ions flow diffusively in a medium driven by an applied electric field. By applying an electrical potential, agents can be selectively absorbed by tissue. The electrically conductive, radially expansible cage 402 is radially expanded to contact the renal pelvis walls and acts as an anode. A nerve affecting agent can then be injected to the site and will be absorbed by the tissue at the mesh/tissue interface. The cathode can be provided by electrodes 404 on the catheter and/or an external cathode pad 406 on the patient's P skin. The cage and the cathodes are connected to a suitable power supply 408.

As shown in FIGS. 38A-38D, a balloon catheter 410 carries a balloon 412 covered by a sheath or jacket formed from a mesh covered by a silicone or other elastomeric material. Silicone sleeves are placed over the proximal and distal ends of the mesh layer. The catheter has a fluid lumen 414 with an exit port adjacent a proximal end of the silicone, between the silicone and the catheter and into the mesh. Fluid is passed through the fluid lumen and flows in between the strands of the mesh which sandwiched between the balloon and the silicone. The fluid then exits the distal end of the proximal silicone and contacts the tissue between the two silicone sleeves. This allows for targeted delivery for nerve affecting agents. This design can also be used in vascular catheters to deliver drugs to vessel walls.

FIGS. 39-42 are images obtained by the inventors showing the renal pelvic nerves to be within 1 mm of the tissue surface. The devices of the present invention are configured to particularly target this depth. As shown in FIGS. 38-42, the ureter is also rich with renal nerves. The devices of the present invention can also be configured to target nerves within the ureter in addition to or as an alternative to nerves in the renal pelvis.

Figure 43:
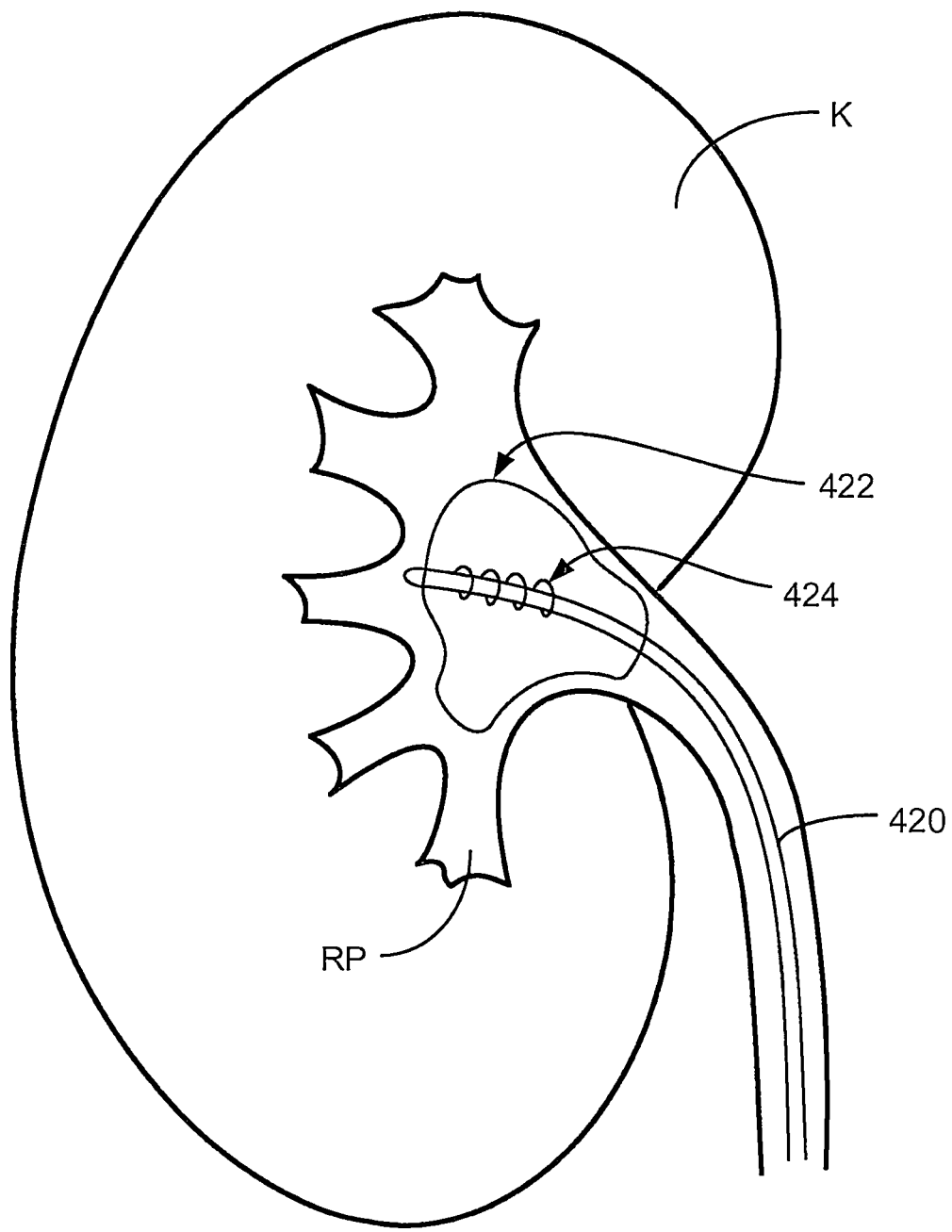
FIG. 43 shows a balloon catheter with heating coil.

As shown a FIG. 43, a catheter 420 carries a compliant or semi-compliant balloon 422 is deployable in the renal pelvis RP. The balloon 422 is inflated with saline or other liquid. The balloon is sufficiently compliant to conform to the anatomy of the renal pelvis to maximize wall contact. A resistive heating coil 424 made from a suitably resistive material, such as Nichrome®, is located inside the balloon. The coil heats the liquid to 60° C., and the balloon is maintained in place for a suitable time period against the wall of the renal pelvis to achieve the desired nerve ablation. Thermocouples located on the catheter and on the coil and inside the balloon can be used to regulate temperature. Alternatively, the liquid can be heated outside the catheter and pumped through the catheter/balloon assembly.

Figure 44A:
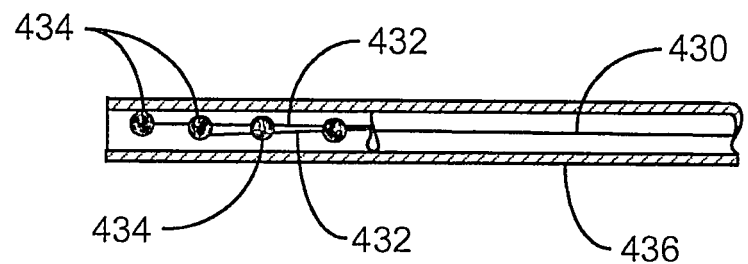
FIGS. 44A and 44B show a bifurcated superelastic alloy wire with ball electrodes.
Figure 44B:
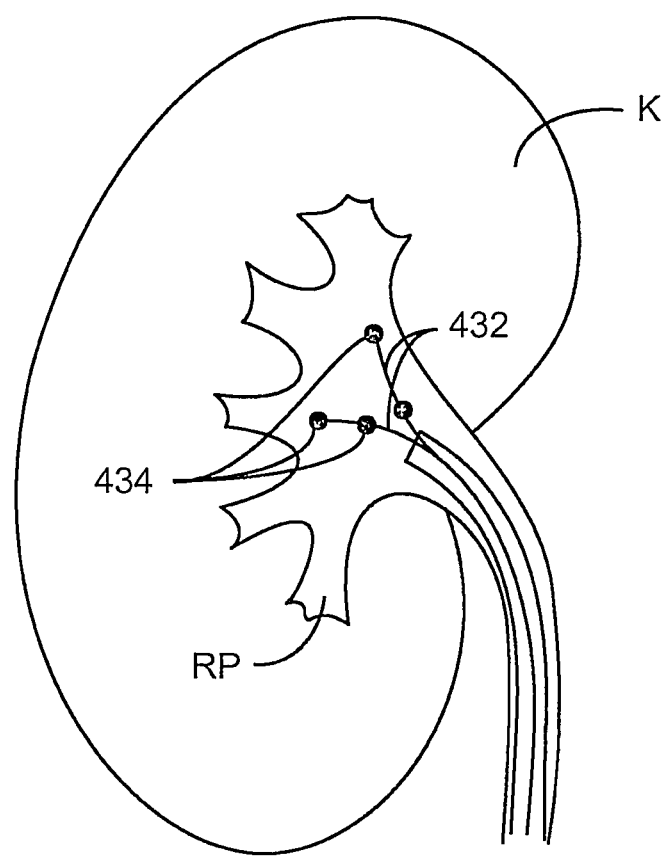

As shown in FIGS. 44A and 44B, a Nitinol® or other superelastic alloy wire 430 is bifurcated into branches 432 its distal end. Ball electrodes 434 are secured to each branch at alternating locations so that the branches can be collapsed within the lumen of a delivery sheath or catheter 436 as shown in FIG. 44A. The branches carrying the electrodes can be deployed out of the catheter and into the renal pelvis RP. The branches are biased apart to achieve spacing of the ball electrodes. RF energy is applied through the wire to the ball electrodes and discreet lesions are formed on the tissue wall. A vacuum can be applied embed the ball electrodes into the tissue surface.

Figure 22:
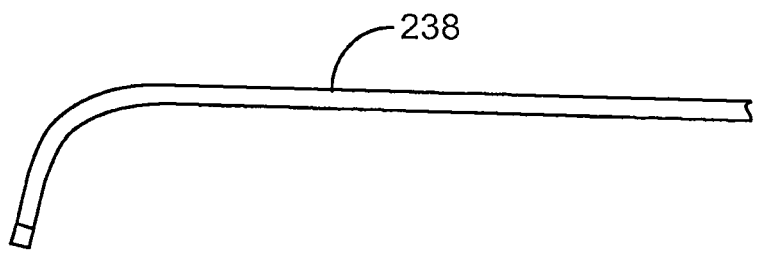
Figure 23:
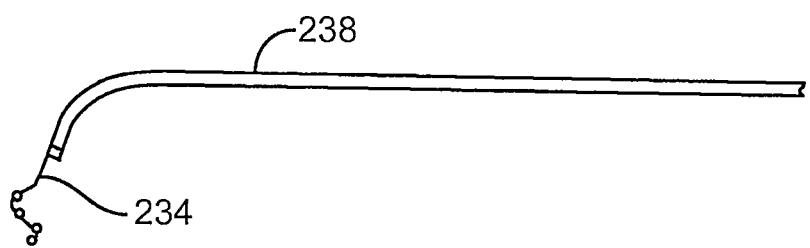
Figure 45:
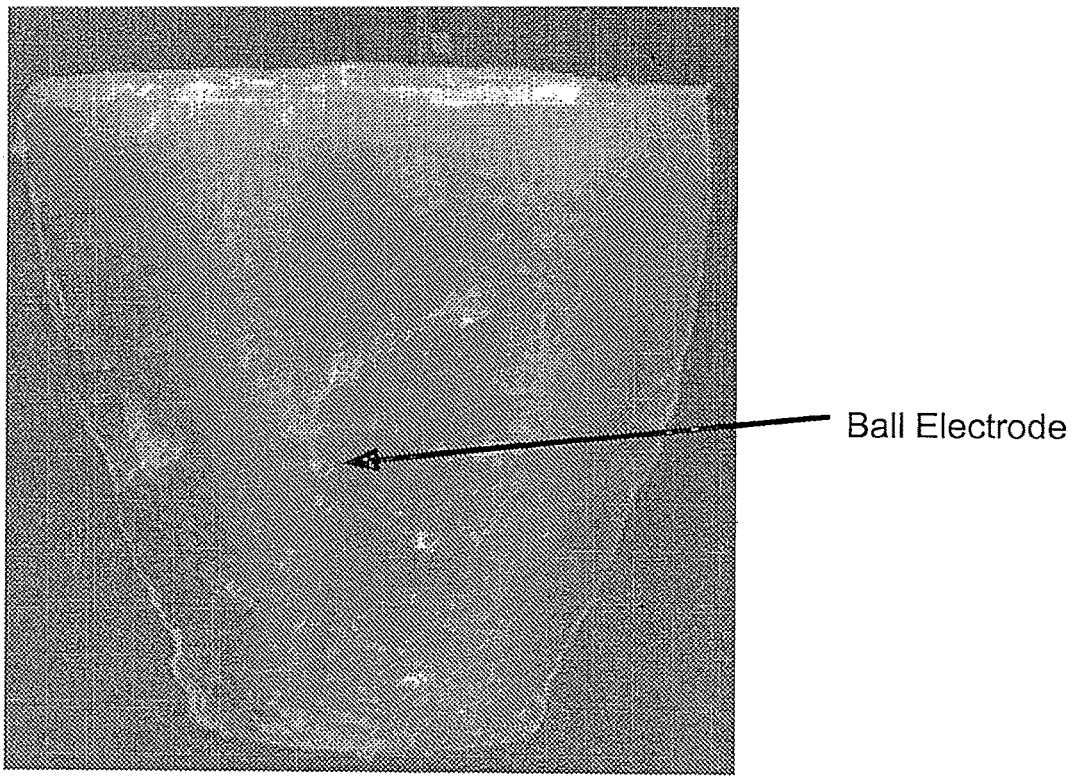
FIG. 45 shows a ball electrode device in temperature sensitive gel.
Figure 46:
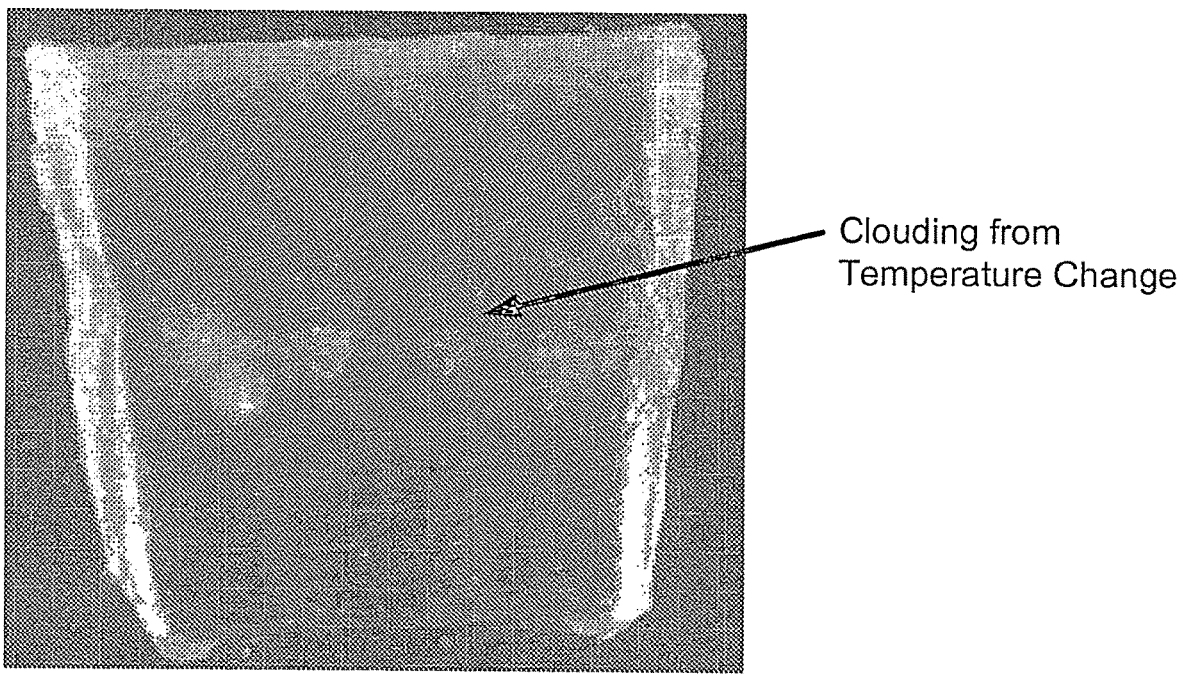
FIG. 46 shows a white clouding of the gel where the temperature was increased over 50° C. from the device.

Applying RF or other heating means to the renal pelvis requires a balance of time and temperature. Too much energy will damage function of the renal pelvis. Not enough energy will prevent effective renal denervation. Experimentation has shown that a temperature in the range from 55° C.

to 65° C., preferably 60° C. applied for time in the range from 1 minute to 3 minutes, preferably 2 minutes, is optimal to achieve ablation of nerves surrounding the renal pelvis and in some cases the ureter. As shown in FIG. 45, ball electrodes are inserted into a gel phantom that mimics tissue electrical and thermal characteristics. The gel changes to a white color when the temperature is brought above 50° C. as shown in FIG. 22.

Many of the above described device designs dilate, stretch, or otherwise tension the wall of the renal pelvis during the application of energy, the mechanical treatment of the renal pelvic wall, or substance delivery. This stretching is advantageous as it thins the tissue wall bringing the nerves closer to the treatment elements, particularly for the delivery of RF current.

What is claimed is:

1. A method for treating hypertension, the method comprising:
   selecting a patient diagnosed with hypertension;
   positioning a distal end of a catheter into an interior of the patient's kidney, wherein the positioning further comprises
      advancing a catheter through a urinary tract of a patient toward a renal pelvis of the patient such that a distal end of the catheter is positioned within the renal pelvis or ureteral pelvic junction adjacent the renal pelvis,
      providing one or more electrodes at the distal end of the catheter, the one or more electrodes being in communication with a radio frequency energy source,
      causing the collapse of a wall of the renal pelvis and contemporaneous removal of fluid, if any, in the kidney such that renal pelvic wall tissue of the renal pelvis comes into contact with the one or more electrodes; and
   delivering an amount of energy through a wall of the kidney to denervate adjacent nerves to treat the hypertension, wherein the delivering further comprises
      applying radio frequency energy to the one or more electrodes to disrupt and/or ablate afferent nerves in the renal pelvic wall tissue proximate the respective locations at which the renal pelvic wall tissue contacts the one or more electrodes,
      wherein applying radio frequency energy disrupts and/or ablates primarily afferent renal nerves contained in the renal pelvic wall tissue,
      whereby, by disrupting and/or ablating the primarily afferent renal nerves, the patient's efferent nerve activity is altered, and
      whereby altering the patient's efferent nerve activity causes a reduction in the patient's blood pressure.

2. The method of claim 1, wherein the energy is radio frequency (RF) energy delivered via one or more flexible wires on the distal end of the catheter.

3. The method of claim 2, wherein the one or more flexible wires are manipulable between a first position wherein the one or more flexible wires are within a lumen, and a second position wherein the one or more flexible wires are extended out of the lumen through an opening.

4. The method of claim 3, wherein the one or more flexible wires are configured to deliver the energy to a renal nerve when the one or more flexible wires are in the second position.

5. The method of claim 2, wherein the catheter is inserted to a first position within a conduit, the first distal end is positioned adjacent to a renal nerve, the one or more flexible wires are through the lumen or the catheter is retracted so that the one or more flexible wires extend out of the lumen through the opening adjacent the renal nerve.

6. The method of claim 1, wherein the radio frequency energy is applied for 1 to 2 minutes.

7. The method of claim 1, wherein the renal pelvic wall tissue containing the afferent renal nerves is heated to a temperature of 45 to 80 degrees Celsius.

8. The method of claim 1, wherein at least a portion of the disrupted and/or ablated afferent renal nerves are located within one or more smooth muscle layers of the renal pelvic wall.

9. The method of claim 1, wherein at least a portion of the disrupted and/or ablated afferent renal nerves are located within an endothelium region of the renal pelvic wall.

10. The method of claim 1, wherein disrupting and/or ablating afferent renal nerves has a direct effect on efferent renal nerve activity.

11. The method of claim 1, wherein applying radio frequency energy forms lesions in renal pelvic wall tissue by raising the temperature of the one or more electrodes to 60 degrees C. for two minutes.

12. The method of claim 1, wherein the patient's renal pelvis contains urine after the positioning step and before the delivering step.

13. The method of claim 2, wherein a vacuum is drawn through a lumen of the catheter.

14. The method of claim 2, wherein collapse of walls of the renal pelvis is partial.

15. The method of claim 2, wherein applying radio frequency energy preferentially disrupts and/or ablates nerves disposed closer to an interior surface of the wall of the renal pelvis than to an exterior surface of the wall of the renal pelvis.

* * * * *